US012558337B2

(12) United States Patent
Lehmann et al.

(10) Patent No.: US 12,558,337 B2
(45) Date of Patent: Feb. 24, 2026

(54) FORMULATIONS COMPRISING MELFLUFEN

(71) Applicant: ONCOPEPTIDES INNOVATION AB, Stockholm (SE)

(72) Inventors: Fredrik Lehmann, Stockholm (SE); Peter Teodorovic, Stockholm (SE)

(73) Assignee: ONCOPEPTIDES INNOVATION AB, Stockholm (SE)

( * ) Notice: Subject to any disclaimer, the term of this patent is extended or adjusted under 35 U.S.C. 154(b) by 1093 days.

(21) Appl. No.: 17/603,762

(22) PCT Filed: Apr. 17, 2020

(86) PCT No.: PCT/EP2020/060900
§ 371 (c)(1),
(2) Date: Oct. 14, 2021

(87) PCT Pub. No.: WO2020/212594
PCT Pub. Date: Oct. 22, 2020

(65) Prior Publication Data

US 2022/0184021 A1 Jun. 16, 2022

(30) Foreign Application Priority Data

Apr. 17, 2019 (GB) ...................................... 1905477

(51) Int. Cl.
*A61K 31/216* (2006.01)
*A61K 45/06* (2006.01)
*A61K 47/10* (2017.01)

(52) U.S. Cl.
CPC ............ *A61K 31/216* (2013.01); *A61K 45/06* (2013.01); *A61K 47/10* (2013.01)

(58) Field of Classification Search
CPC .............................. A61K 47/10; A61K 31/216
See application file for complete search history.

(56) References Cited

U.S. PATENT DOCUMENTS

| | | | | |
|---|---|---|---|---|
| 10,285,946 | B2 * | 5/2019 | Spira | A61K 47/10 |
| 10,322,182 | B2 * | 6/2019 | Spira | A61P 35/00 |
| 10,869,928 | B2 * | 12/2020 | Spira | A61K 38/05 |
| 11,896,668 | B2 * | 2/2024 | Spira | A61K 9/19 |
| 12,152,087 | B2 * | 11/2024 | Lehmann | C07K 5/06191 |
| 2004/0097421 | A1 | 5/2004 | Lewensohn et al. | |

FOREIGN PATENT DOCUMENTS

| | | | | |
|---|---|---|---|---|
| DE | 0159289 Z | 3/1983 | | |
| WO | 2001/096367 A1 | 12/2001 | | |
| WO | 2011/078782 A1 | 6/2011 | | |
| WO | WO-2012146625 A1 * | 11/2012 | | A61K 31/195 |
| WO | 2014/065751 A1 | 5/2014 | | |
| WO | 2017/093443 A1 | 6/2017 | | |
| WO | WO-2019185859 A1 * | 10/2019 | | A61K 31/192 |
| WO | 2020/079165 A1 | 4/2020 | | |

OTHER PUBLICATIONS

Haskins, "The Application of Stable Isotopes in Biomedical Research", 1982, Biomedical Mass Spectrometry, 9, pp. 269-277 (Year : 1982).*
Browne, "Stable Isotope Techniques in Early Drug Development", 1998, J Clin Pharmacol, 38, pp. 213-220 (Year: 1998).*
Carlier et al., "Preclinical activity of melflufen (J1) in ovarian cancer", 2016, Oncotarget, 7, pp. 59322-59335 (Year: 2016).*
International Search Report and Written Opinion issued Jun. 19, 2020 in PCT/EP2020/060900.
Gullbo et al., 2003, "Activity of Hydrolytic Enzymes in Tumour Cells is a Determinant for Anti-tumor Efficacy of the Melphalan Containing Prodrug J1" J. Drug Target., 11: 355-363.
Wickstrom et al., 2010, "The alkylating prodrug J1 can be activated by aminopeptidase N, leading to a possible target directed release of melphalan" Biochem. Pharmacol., 79: 1281-1290.
Wickstrom et al., 2017 "Melflufen—a peptidase-potentiated alkylating agent in client trials" Oncotarget 8(39): 66641-66655.
Third Party Observations with respect to European Patent Application No. 20722234.0-1112 dated Oct. 10, 2024.
EPO Office Action issued in EPO Patent Application No. 20722234.0 on Jan. 31, 2023.
EPO Office Action issued in EPO Patent Application No. 20722234.0 on Feb. 22, 2024.

* cited by examiner

*Primary Examiner* — Brenda L Coleman
*Assistant Examiner* — Madeline E Braun
(74) *Attorney, Agent, or Firm* — Biospark Intellectual Property Law

(57) ABSTRACT

The invention provides a pharmaceutical formulation comprising (or consisting essentially of) the following components: i) melflufen, or a salt thereof; ii) propylene glycol; iii) optionally one or more physiologically acceptable aqueous solvent(s); and iv) optionally one or more additional therapeutic agent(s); or a pharmaceutical formulation comprising (or consisting essentially of) the following components: i) melflufen, or a salt thereof; ii) polyethylene glycol; iii) optionally one or more physiologically acceptable aqueous solvent(s); and iv) optionally one or more additional therapeutic agent(s). The invention also provides methods for preparing the pharmaceutical formulations of the invention, kits and uses of the pharmaceutical formulations of the invention.

18 Claims, 9 Drawing Sheets

FORMULATIONS COMPRISING MELFLUFEN

FIELD OF THE INVENTION

The present invention relates to novel pharmaceutical formulations containing melflufen, or a salt thereof, and their use. The present invention also provides kits and methods for preparing the novel pharmaceutical formulations of the invention.

BACKGROUND OF THE INVENTION

Melflufen (also known as melphalan flufenamide and L-Melphalanyl-4-fluoro-L-phenylalanine ethyl ester), is an anti-tumour agent useful in the treatment of cancer, particularly the treatment of multiple myeloma. Melflufen is described in WO 01/96367 and WO 2014/065751. The structure of the hydrochloride salt of melflufen is shown below:

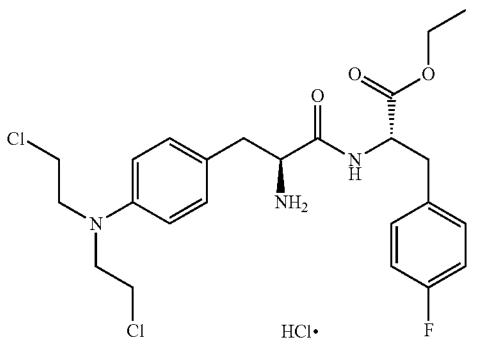

Melflufen is a potent and highly lipophilic alkylating agent and it achieves targeted delivery of alkylating metabolites to tumour cells. In contrast to other alkylating agents that are hydrophilic, the high lipophilicity of melflufen leads to its rapid uptake into tissues and cells. Once inside a cell, melflufen may bind directly to DNA or it may be readily hydrolysed by intracellular peptidases into melphalan or hydrolysed by intracellular esterases into des-ethylmelflufen (this compound may alternatively be referred to as L-Melphalanyl-4-fluoro-L-phenylalanine), which also has alkylating properties. The high activity of esterases and peptidases in human tumours is postulated to lead to the rapid formation of melflufen's metabolites in these cells which then leads to inflow of more melflufen (Gullbo, J., et al, J Drug Target, (2003) Vol 11, pages 355-363; Wickstrom, M., et al, Biochem Pharmacol (2010) Vol 79, pages 2381-1290). Since des-ethylmelflufen and melphalan are relatively hydrophilic, there is a possibility for intracellular trapping of these agents.

Melflufen is generally provided in crystalline form after synthesis. The crystalline form can only be dissolved in highly acidic aqueous solutions that are often unsuitable for manufacturing and pharmaceutical purposes. In previous pharmaceutical preparations, the crystalline form was dissolved in a dimethylacetamide (DMA) and glucose solution. However, this preparation was unstable and readily formed unwanted melflufen dimers. Organic solvents, such as DMA, can also be hazardous to patients and can damage medical devices used for administration. Stable lyophilised preparations of melflufen are described in WO 2014/065751 and display advantageous stability and dissolution characteristics.

There is still an unmet need for liquid pharmaceutical formulations of melflufen, or salts thereof, that display beneficial stability and handling properties.

SUMMARY OF THE INVENTION

The present invention provides a pharmaceutical formulation comprising (or consisting essentially of) the following components:

i) melflufen, or a salt thereof;
ii) propylene glycol;
iii) optionally one or more physiologically acceptable aqueous solvent(s); and
iv) optionally one or more additional therapeutic agent(s).

Preferably, the melflufen, or salt thereof, contained in the pharmaceutical formulation of the invention is dissolved in the pharmaceutical formulation. The present inventors have found that melflufen and salts thereof, are surprisingly soluble in propylene glycol, such that more concentrated solutions can be prepared than with previously used solvents. Furthermore, the present inventors have found that when melflufen, or a salt thereof, is stored in the form of a pharmaceutical formulation containing propylene glycol, the melflufen, or salt thereof, is surprisingly stable and does not readily form unwanted degradations products. Notably, in a stability study, a pharmaceutical formulation containing a hydrochloride salt of melflufen (OPD-5) and propylene glycol was found to retain a melflufen purity of greater than 95% (relative to the melflufen purity before storage of the formulation) when stored at about 5° C. (i.e. 5±3° C. (2 to 8° C.)) for over 50 days. In a further stability study, a pharmaceutical formulation containing a hydrochloride salt of melflufen (OPD-5) and propylene glycol was found to be stable for at least 6 months when stored at −20° C. and for at least 8 months when stored at −70° C. In addition, the present inventors also found that pharmaceutical formulations containing an ethanesulfonic acid, p-toluenesulfonic acid or hydrochloric acid salt of melflufen and propylene glycol, retained a melflufen purity of greater than 90% (relative to the melflufen purity before storage of the formulation) when stored at room temperature (i.e. 20-25° C.) for 4 weeks (28 days), and retained a melflufen purity of greater than 85% after 7 weeks (49 days) of storage at room temperature.

The present invention provides a pharmaceutical formulation comprising (or consisting essentially of) the following components:

i) melflufen, or a salt thereof;
ii) polyethylene glycol (PEG);
iii) optionally one or more physiologically acceptable aqueous solvent(s); and
iv) optionally one or more additional therapeutic agent(s).

Preferably, the melflufen, or salt thereof, contained in the pharmaceutical formulation of the invention is dissolved in the pharmaceutical formulation. The present inventors have found that melflufen and salts thereof, are surprisingly soluble in PEG, such that more concentrated solutions can be prepared than with previously used solvents. Furthermore, the present inventors have found that when melflufen, or a salt thereof, is stored in the form of a pharmaceutical formulation containing PEG, the melflufen, or salt thereof, is surprisingly stable and does not readily form unwanted degradations products. Notably, in a stability study, a pharmaceutical formulation containing PEG was found to retain a melflufen purity of greater than 95% (relative to the melflufen purity before storage of the formulation) when stored at about 5° C. (i.e. 5±3° C. (2 to 8° C.)) for over 50 days.

The present invention further provides a pharmaceutical formulation of the invention for use as a medicament.

The present invention further provides a pharmaceutical formulation of the invention for use in the treatment or prophylaxis of a disease or condition that may be treated with conventional chemotherapy agents, for example, with an alkylator (e.g. melphalan, cyclophosphamide and bendamustine).

The present invention further provides a pharmaceutical formulation of the invention for use in the treatment or prophylaxis of cancer, for example a cancer selected from the list consisting of multiple myeloma, breast cancer, lung cancer, ovarian cancer, leukaemias and lymphomas.

The present invention further provides a pharmaceutical formulation of the invention for use in the treatment or prophylaxis of amyloidosis.

The present invention further provides a method for treating a patient which comprises the step of administering a pharmaceutically effective amount of the pharmaceutical formulation of the invention to a subject.

The pharmaceutical formulations of the invention may be administered directly to a subject, for example without the need for prior dilution, for example, prior dilution with a physiologically acceptable solvent or diluent. Thus, in one preferred embodiment of the invention the pharmaceutical formulation is directly administered to a patient. In an alternative embodiment, the pharmaceutical formulation is administered to a patient following dilution, for example following dilution with a physiologically acceptable solvent or diluent, for example a saline solution, a glucose solution, or a mixture thereof.

The present invention further provides a method for preparing a pharmaceutical formulation of the invention comprising the step of dissolving melflufen, or a salt thereof, in propylene glycol.

The present invention further provides a method for preparing a pharmaceutical formulation of the invention comprising the step of dissolving melflufen, or a salt thereof, in PEG.

The present invention further provides a method for storing melflufen, or a salt thereof, comprising the steps of preparing a pharmaceutical formulation of the invention and storing the pharmaceutical formulation at a temperature of −90 to 25° C. Preferably, the pharmaceutical formulation of the invention is stored at a temperature of about 5° C. or less, for example about 0 to 4° C., about −20° C. and about −80° C.

The present invention further provides a kit comprising melflufen, or a salt thereof; propylene glycol; optionally one or more physiologically acceptable aqueous solvent(s); and optionally one or more additional therapeutic agent(s).

The present invention further provides a kit comprising melflufen, or a salt thereof; PEG; optionally one or more physiologically acceptable aqueous solvent(s); and optionally one or more additional therapeutic agent(s).

DETAILED DESCRIPTION

Figure 1:
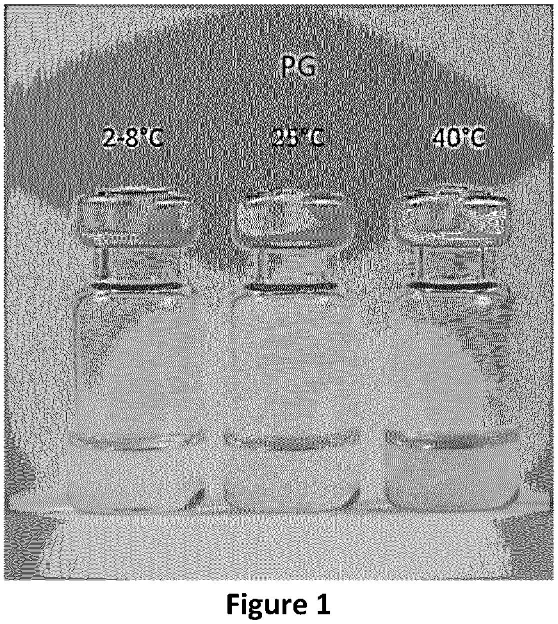
FIG. 1 shows the visual appearance of a pharmaceutical formulation consisting essentially of melflufen (ODP-5) and propylene glycol (the "PG formulation") following storage for 31 days ($T_1$) at 2-8° C., 25° C. or 40° C. The samples stored at 2-8° C. have no visible colouration. The samples stored at 25° C. and 40° C. have a yellow to brown colouration.

As described in further detail below, the present invention provides pharmaceutical formulations of melflufen, and salts thereof, that are surprisingly stable and that display advantageous handling properties.

Melflufen and Salts Thereof

For the avoidance of doubt, in this document, when the term "melflufen" is used, it is also intended to include salt(s) thereof, even if this is not explicitly stated.

Also for the avoidance of doubt, in this document, when the term "melflufen" is used, it includes isotopic derivatives of melflufen, unless stated otherwise. Particular examples of isotopic derivatives of melflufen suitable for use in the present invention are deuterated melflufen derivatives. Examples of deuterated melflufen derivatives, and methods of making deuterated melflufen derivatives, are described in PCT/EP2019/078250, the content of which is incorporated herein by reference.

For example, a deuterated melflufen derivative suitable for use in the present invention may be a compound of formula (I), or a pharmaceutically acceptable salt thereof, Formula (I)

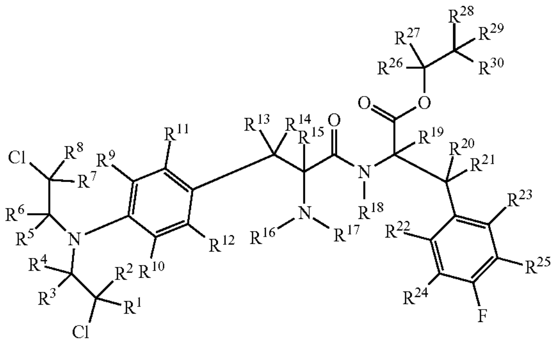

wherein, each $R^1$-$R^{30}$ is independently selected from the group consisting of H and deuterium, and at least one of $R^1$-$R^{30}$ is deuterium with an abundance level greater than the naturally occurring abundance of deuterium (for example wherein at least one of $R^1$-$R^{30}$ has a deuterium abundance level of at least 1 mol %, 5 mol %, 10 mol %, 50 mol %, 90 mol % or 98 mol % deuterium, e.g. at least 10 mol %, 50 mol %, 90 mol % or 98 mol % deuterium). For example at least one of $R^1$-$R^8$ is deuterium with an abundance level of at least 5 mol %; or at least one of $R^9$-$R^{15}$ is deuterium with an abundance level of at least 5 mol %; or at least one of $R^{16}$-$R^{18}$ is deuterium with an abundance level of at least 5 mol %; or at least one of $R^{19}$-$R^{25}$ is deuterium with an abundance level of at least 5 mol %; or at least one of $R^{26}$-$R^{30}$ is deuterium with an abundance level of at least 5 mol % (e.g. at least two of $R^{26}$-$R^{30}$ is deuterium, for example wherein two of $R^{26}$-$R^{30}$ are deuterium; or wherein three of $R^{26}$-$R^{30}$ are deuterium; or wherein four of $R^{26}$-$R^{30}$ are deuterium; or wherein each of $R^{26}$-$R^{30}$ are deuterium).

Preferably, a deuterated melflufen derivative of formula (I), and/or a deuterated melflufen derivative described below, has the stereochemistry of melflufen shown in the structure of melflufen on page 1 of the present specification.

In certain embodiments, a deuterated melflufen derivative suitable for use in the present invention has a structural formula selected from the following group:

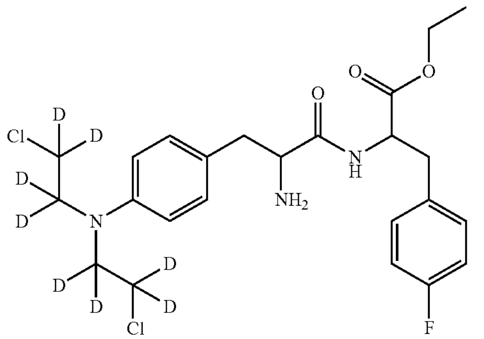

-continued

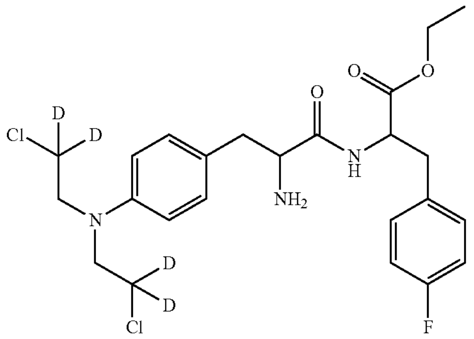

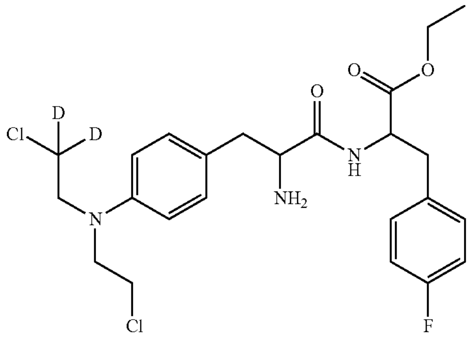

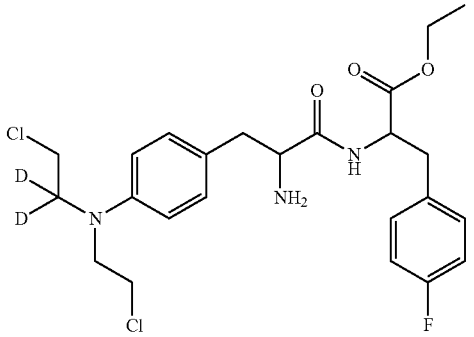

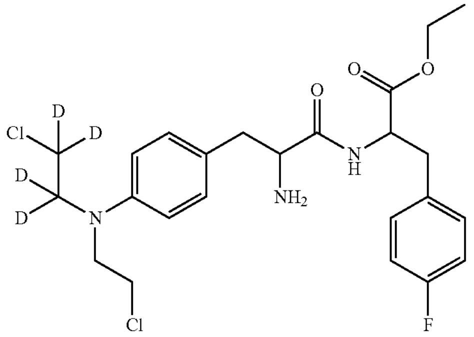

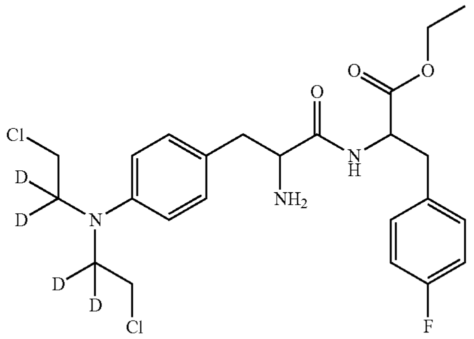

-continued
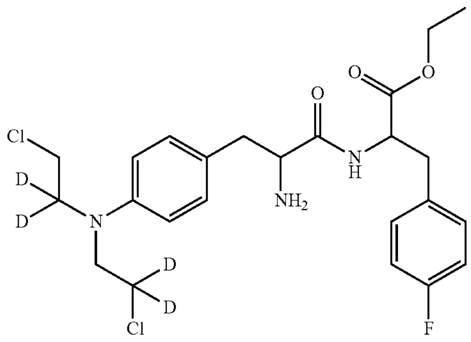
or a structural formula selected from the following group:
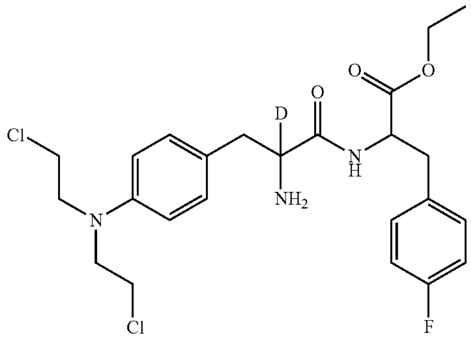
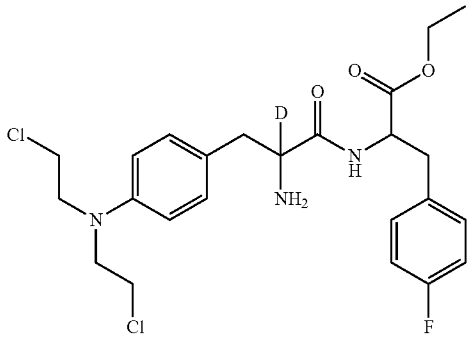
or a structural formula selected from the following group:
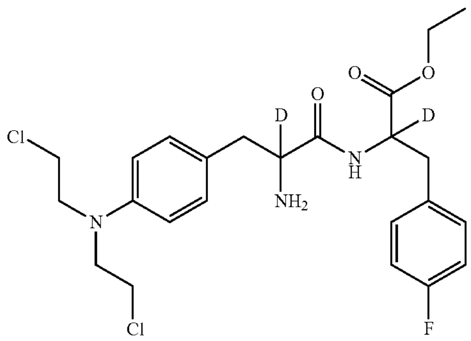
-continued
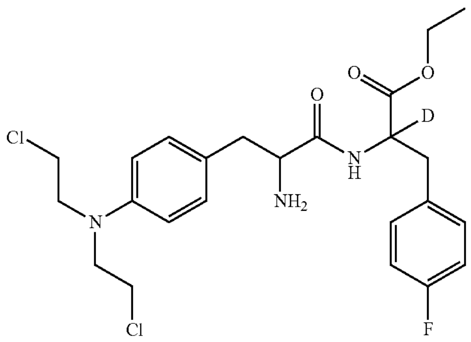
or a structural formula selected from the following group:
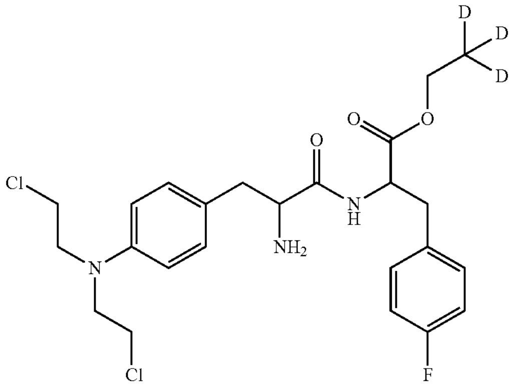
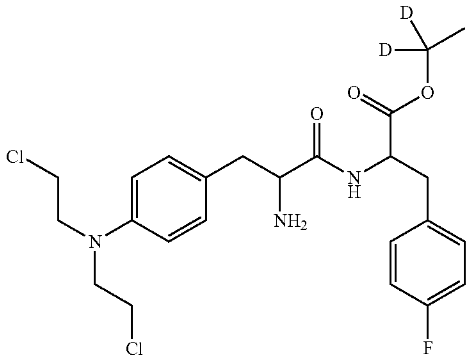
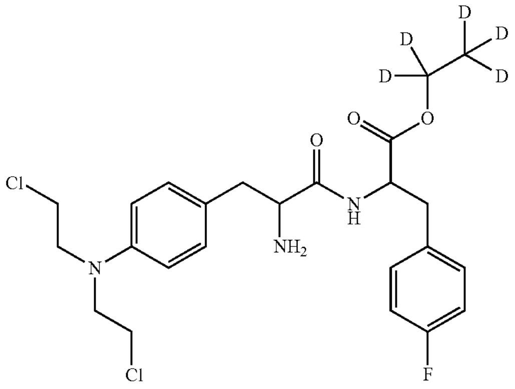
In certain embodiments, a deuterated melflufen derivative suitable for use in the present invention is OPD-5, which has the following structure:

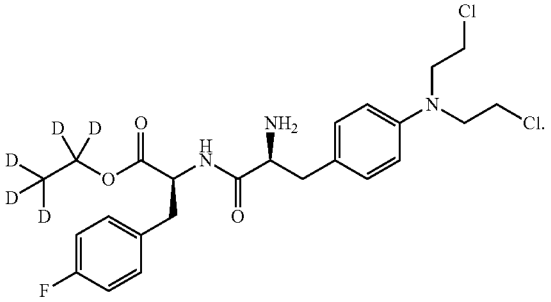 [SMILES: [2H]C([2H])([2H])C([2H])([2H])OC(=O)[C@H](Cc1ccc(F)cc1)NC(=O)[C@@H](N)Cc1ccc(N(CCCl)CCCl)cc1]

In certain embodiments, a deuterated melflufen derivative suitable for use in the present invention is selected from the following group:

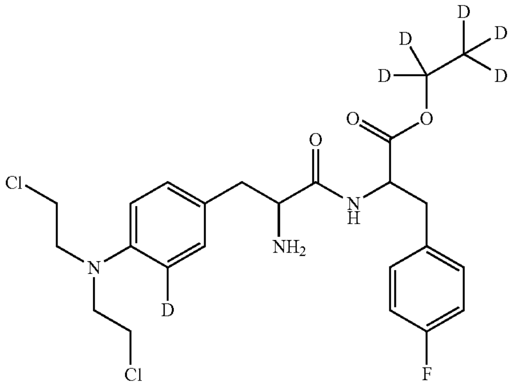

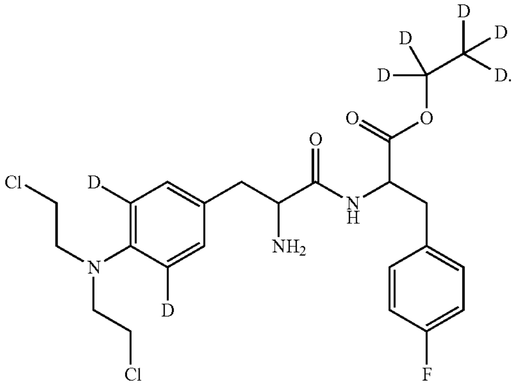

Also for the avoidance of doubt, when referred to in this document, the mass of melflufen is the mass of the melflufen molecule excluding the mass of any counterion unless explicitly stated otherwise. The molecular weight of counterion-free melflufen (with a natural isotope abundance) is 498.42 g/mol. Melflufen, and salts thereof, especially the hydrochloride salt thereof, are known from, for example, WO 01/96367 and WO 2014/065751, and the same salts are suitable for use in the present invention.

Salts of melflufen which are suitable for use in the present invention are those wherein a counterion is pharmaceutically acceptable. Suitable salts include those formed with organic or inorganic acids. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$) alkyl or aryl sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxalic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

Preferred salts of melflufen include acid addition salts such as those formed from hydrochloric, hydrobromic, acetic, p-toluenesulfonic, tartaric, sulphuric, succinic, phosphoric, oxalic, nitric, methanesulfonic, malic, maleic and citric acid. More preferably, the salt of melflufen for use according to the present invention is the hydrochloride salt (i.e. the addition salt formed from hydrochloric acid).

Other preferred salts of melflufen include hydrochloric, hydrobromic, nitric, methansulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid.

In another embodiment, preferred salts of melflufen include acid addition salts such as those formed from hydrochloric, hydrobromic, acetic, p-toluenesulfonic, tartaric, sulphuric, succinic, phosphoric, oxalic, nitric, methanesulfonic, malic, maleic, citric or ethanesulfonic acid. Preferably, the salt of melflufen for use according to the present invention is the hydrochloride salt (i.e. the addition salt formed from hydrochloric acid), ethanesulfonate salt (i.e. the addition salt formed from ethanesulfonic acid), hydrobromide salt (i.e. the addition salt formed from hydrobromic acid), maleate salt (i.e. the addition salt formed from maleic acid), or p-toluenesulfonate salt (the addition salt formed from p-toluenesulfonic acid).

In another preferred embodiment, the salt of melflufen for use according to the present invention is the hydrochloride salt (i.e. the addition salt formed from hydrobromic acid), ethanesulfonate salt (i.e. the addition salt formed from ethanesulfonic acid), maleate salt (i.e. the addition salt formed from maleic acid), or p-toluenesulfonate salt (the addition salt formed from p-toluenesulfonic acid) (for example, the hydrochloride salt, ethanesulfonate salt or p-toluenesulfonate salt).

More preferably, the salt of melflufen is the ethanesulfonate salt or the hydrochloride salt.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". The complex may incorporate a solvent in stoichiometric or non-stoichiometric amounts. Solvates are described in Water-Insoluble Drug Formulation, $2^{nd}$ ed R. Lui CRC Press, page 553 and Byrn et al Pharm Res 12(7), 1995, 945-954. Before it is made up in solution, the melflufen, or salt thereof, for use in the present invention may be in the form of a solvate. Solvates of melflufen that are suitable for use according to the present invention are those wherein the associated solvent is pharmaceutically acceptable. For example a hydrate is a pharmaceutically acceptable solvate.

Formulations

The present invention provides a pharmaceutical formulation as defined above.

The pharmaceutical formulations of the invention are particularly suitable for long-term storage of melflufen, and salts thereof. Long-term storage is understood to mean that the pharmaceutical formulation can be stored for 1 to 3 months, 3 to 6 months, 6 to 9 months, 9 to 12 months, or more, without the melflufen purity decreasing by more than 0% to 5%, 5% to 10%, 10% to 15% or 15% to 20%, relative to the melflufen purity of the formulation at the beginning of storage.

For long-term storage, the pharmaceutical formulation of the invention is stored at a temperature below 10° C., for example 5° C. (for example, 5±3° C.) or less. Preferably, the pharmaceutical formulation of the invention is stored at a temperature below 0° C., for example 0 to −30° C., −30 to −60° C. or −60 to −90° C. More preferably, the pharmaceutical formulation of the invention is stored at −15 to −25° C. or −75 to −85° C.

In a preferred embodiment of the invention, the pharmaceutical formulation of the invention comprises (or consists essentially of) melflufen, or a salt thereof, and propylene glycol.

In another preferred embodiment of the invention, the pharmaceutical formulation of the invention consists essentially of melflufen, or a salt thereof, and propylene glycol.

In another preferred embodiment of the invention, the pharmaceutical formulation of the invention comprises (or consists essentially of) melflufen, or a salt thereof, and PEG.

In another preferred embodiment of the invention, the pharmaceutical formulation of the invention consists essentially of melflufen, or a salt thereof, and PEG.

Preferably, the PEG has an average molecular weight of 150 to 650 Da, for example 150 to 250, 250 to 350, 350 to 450, 450 to 550, and 550 to 650 Da. For example, the PEG may be PEG 200, PEG 300, PEG 400 or PEG 600 as defined in national pharmacopoeias. More preferably, the PEG has an average molecular weight of 250 to 350 Da. Even more preferably the PEG is PEG 300.

In another embodiment of the invention, the pharmaceutical formulation of the invention comprises (or consists essentially of) melflufen, or a salt thereof, and PEG, wherein the PEG content is formed from a mixture of two or more different PEG compounds, for example a mixture comprising one or more of PEG 200, PEG 300, PEG 400 and PEG 600.

In another embodiment of the invention, the pharmaceutical formulation of the invention consists essentially of melflufen, or a salt thereof, and PEG, wherein the PEG content is formed from a mixture of two or more different PEG compounds, for example a mixture comprising one or more of PEG 200, PEG 300, PEG 400 and PEG 600.

In another embodiment of the invention, the pharmaceutical formulation of the invention comprises (or consists essentially of) melflufen, or a salt thereof, propylene glycol and PEG.

In another embodiment of the invention, the pharmaceutical formulation of the invention consists essentially of melflufen, or a salt thereof, propylene glycol and PEG.

In embodiments of the invention wherein the pharmaceutical formulation contains PEG and propylene glycol, the PEG content may be formed from one PEG compound as described above, or formed from a mixture of two or more different PEG compounds, as described above.

For pharmaceutical formulations of the invention containing PEG and propylene glycol, the weight ratio (w/w) of the PEG and propylene glycol content may be, for example, about 0.5:1, 1:1, 1:2, 1:5, 1:10, 1:15, 1:20, 1:25, 1:30, 1:35, 1:40, 1:45, 1:50, 1:0.5, 2:1, 5:1, 10:1, 15:1, 20:1, 25:1, 30:1, 35:1, 40:1, 45:1 or 50:1.

Propylene glycol and PEG suitable for use according to the invention are readily available from commercial sources.

Preferred embodiments of the pharmaceutical formulations of the invention do not contain an additional physiologically acceptable solvent (iii).

The pharmaceutical formulations of the invention may optionally contain one or more physiologically acceptable aqueous solvents. Suitable aqueous solvents include non-toxic, parenterally acceptable diluents or solvents, such as water, Ringer's solution, glucose solution and sodium chloride solutions (for example, isotonic sodium chloride solutions).

The pharmaceutical formulations of the invention may further optionally contain additional components such as anti-oxidants, buffering agents, bacteriostats, and solutes which render the pharmaceutical formulation of the invention isotonic with the blood of the intended recipient.

In one preferred embodiment of the invention, the pharmaceutical formulation of the invention is substantially free from organic solvents that are not PEG or propylene glycol. The term "substantially free" from organic solvents is used herein to mean that the pharmaceutical formulation of the invention only comprises trace amounts of an organic solvent, other than propylene glycol and PEG. For example, less than about 1% w/v of an organic solvent other than propylene glycol or PEG. Preferably less than 0.5% w/v, and more preferably less than 0.1% w/v of an organic solvent other than propylene glycol and PEG.

In one preferred embodiment, the pharmaceutical formulation of the invention is substantially free from an alkaline earth metal salt. Alkaline earth metal salts include beryllium, magnesium, calcium, strontium, barium, and radium salts. Preferably, the pharmaceutical formulation of the invention is substantially free from calcium and/or magnesium salts. The anion of the alkaline earth metal salt may be gluconate, chloride acetate, lactate or bromide. For example, the alkaline earth metal salts may be calcium chloride or magnesium chloride. The term "substantially free from an alkaline earth metal salt" is used herein to mean that the pharmaceutical formulation of the invention only comprise trace amounts of an earth metal salts. For example, less than about 1% w/v of an earth metal salt. Preferably less than 0.5% w/v, and more preferably less than 0.1% w/v of an earth metal salt.

The pharmaceutical formulations of the invention contain melflufen at a concentration of about 1 mg/mL to about 50 mg/mL. For example, 1 to 5, 5 to 10, 10 to 15, 15 to 20, 20 to 25, 25 to 30, 30 to 35, 35 to 40 to 45 and 45 to 50 mg/mL. Preferably, melflufen is at concentration of about 10 to 30 mg/mL. More preferably 15 to 25 mg/mL, for example 15, 16, 17, 18, 19, 20, 21, 22, 23, 24 and 25 mg/mL.

Due to the surprisingly high solubility of melflufen in propylene glycol, and PEG, it is possible to prepare a pharmaceutical formulation according to the invention that has a therapeutically useful concentration of melflufen, or salt thereof. Thus, it is one advantage of the present invention that melflufen, or a salt thereof, is at a concentration that enables the administration of a high dose (for example, a single high dose of about 150 to 800 mg (excluding the mass of any counterion)) of melflufen, or salt thereof, to a subject in a volume that is physiologically acceptable and well-tolerated by the subject.

Whilst melflufen, or a salt thereof, may be present in the pharmaceutical formulation of the invention as the sole active ingredient, it is also possible for the pharmaceutical formulation of the invention to additionally contain one or more additional therapeutic agent(s). Such agents are known in the art. Examples of further therapeutic agents for use in the present invention include steroids (prednisone, prednisolone and dexamethasone), IMiDs (thalidomide, lenalidomide and pomalidomide), PIs (bortezomib, carfilzomib and ixazomib), histone deacetylase (HDAC) inhibitors (panobinostat), conventional chemotherapy (alkylators (e.g. melphalan, cyclophosphamide, bendamustine), doxorubicin), anti-CD38 antibodies (daratumumab) and anti-SLAMF7 antibodies (elotuzumab).

Thus, in one embodiment of the invention, the pharmaceutical formulation of the invention comprises (or consists essentially of) melflufen, or a salt thereof, propylene glycol, and optionally one or more additional therapeutic agent(s).

In another embodiment of the invention, the pharmaceutical formulation of the invention consists essentially of melflufen, or a salt thereof, propylene glycol, and optionally one or more additional therapeutic agent(s).

In another embodiment of the invention, the pharmaceutical formulation of the invention comprises (or consists essentially of) melflufen, or a salt thereof, PEG, and optionally one or more additional therapeutic agent(s).

In another embodiment of the invention, the pharmaceutical formulation of the invention consists essentially of melflufen, or a salt thereof, propylene glycol, PEG, and optionally one or more additional therapeutic agent(s).

The precise quantity and concentration of the additional therapeutic agent that may be present in a pharmaceutical formulation of the invention may vary with the dosing schedule, the potency of the particular agent chosen, the age, size, sex and condition of the subject (typically a mammal, for example a human), the nature and severity of the disease or condition, and other relevant medical and physical factors. The skilled person can readily determine the quantity and concentration of the melflufen, or salt thereof, and optional one or more additional therapeutic agent(s) suitable for use according to the present invention.

Treatments

The pharmaceutical formulations of the present invention find use as medicaments.

In one embodiment of the invention, the pharmaceutical formulations of the invention find use in the treatment and/or prophylaxis of diseases or conditions that may be treated with conventional chemotherapy agents, for example, with an alkylator (e.g. melphalan, cyclophosphamide and bendamustine).

In another embodiment of the invention, the pharmaceutical formulations of the invention find use in the treatment and/or prophylaxis of cancer, reducing tumour growth and/or killing tumour cells. Thus, the pharmaceutical formulations of the invention may be used for curing and/or prolonging the survival of patients afflicted with cancer diseases.

In another embodiment of the invention, the pharmaceutical formulations of the invention find use in the treatment and/or prophylaxis of amyloidosis.

The amount of melflufen which is required to achieve a therapeutic effect will vary with particular route of administration and the characteristics of the subject under treatment, for example the species, age, weight, sex, medical conditions, the particular disease and its severity, and other relevant medical and physical factors. An ordinarily skilled physician can readily determine and administer the effective amount of melflufen required for treatment or prophylaxis of cancer.

The pharmaceutical formulations of the invention find utility in a method for treating a subject which comprises administering a pharmaceutically effective amount of a pharmaceutical formulation of the invention to a subject. Preferably, the pharmaceutical formulation of the invention is administered directly to the subject, for example without prior dilution, for example without prior dilution with a physiologically acceptable solvent or diluent.

The pharmaceutical formulations of the invention may be administered to a subject immediately after preparation or following storage, for example, following storage for 1 to 3 months, 3 to 6 months, 6 to 9 months, 9 to 12 months, or more, as described herein.

Extemporaneous injection and infusion solutions and suspensions may be prepared using a pharmaceutical formulation of the invention. Exemplary compositions for parenteral administration include injectable solutions or suspensions which can contain, for example, suitable non-toxic, physiologically acceptable solvents or diluents (for example, parenterally acceptable solvents or diluents), such as mannitol, glucose, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

In one embodiment of the invention, the pharmaceutical formulation of the invention is administered to the subject following dilution, for example following dilution with a physiologically acceptable solvent or diluent (for example, parenterally acceptable solvent or diluent), such as a saline solution, a glucose solution, or a mixture thereof. Preferably, the physiologically acceptable solvent is a glucose solution (such as about 4.5-5.5 wt % glucose, e.g. about 5 wt % glucose), a saline solution (such as about 0.9 wt % NaCl), or a mixture thereof. Any such solution may optionally be buffered. For example, the pharmaceutical formulation may be diluted with a physiologically acceptable solvent, for example to a melflufen concentration of about 0.001 mg/mL to 1.2 mg/mL (for example 0.01 mg/mL to 1.2 mg/mL, 0.05 mg/mL to 1.2 mg/mL, 0.05 mg/mL to 1.0 mg/mL, 0.05 mg/mL to 0.5 mg/mL, 0.1 mg/mL to 0.4 mg/mL, or 0.1 mg/mL to 0.3 mg/mL), such as about 0.2 mg/ml, before administration to a subject.

Unit Doses

The pharmaceutical formulations of the invention may be provided as unit doses. Preferred unit doses are those containing a requisite dose of melflufen, or salt thereof, suitable for use according to the present invention.

In a preferred embodiment of the invention, the pharmaceutical formulations of the invention may be provided in a vial containing a unit dose of melflufen, or salt thereof. For example, the pharmaceutical formulation of the invention may be provided in a vial containing a unit dose of 10 to 800 mg of melflufen (excluding the mass of any counterion), for example, the vial may contain a unit dose of 50 to 150, 150 to 250, 250 to 350, 350 to 450, 450 to 550, 550 to 650, or 650 to 750 mg of melflufen (excluding the mass of any counterion). Preferably, the vial contains a unit dose of 75 to 125, 125 to 175, or 175 to 225 mg of melflufen, for example 100, 150 and 200 mg of melflufen (excluding the mass of any counterion). More preferably, the vial contains a unit dose of 100 mg of melflufen (excluding the mass of any counterion). In one embodiment, the vial contains a unit dose of 20 mg of melflufen (excluding the mass of any counterion). In one embodiment, the vial contains a unit dose of 40 mg of melflufen (excluding the mass of any counterion).

Methods of Preparation and Storage

The present invention provides a method for preparing a pharmaceutical formulation of the invention.

In a preferred embodiment of the invention, the method for preparing a pharmaceutical formulation of the invention comprises the step of dissolving melflufen, or a salt thereof, in propylene glycol.

In one embodiment of the invention, the method of the invention comprises the additional step of dissolving one or more further therapeutic agents in the propylene glycol, such that the pharmaceutical formulation comprises (or consists essentially of) melflufen, or a salt thereof, propylene glycol, and one or more further therapeutic agents as described herein.

In another preferred embodiment of the invention, the method for preparing a pharmaceutical formulation of the invention comprises the step of dissolving melflufen, or a salt thereof, in PEG. The PEG is preferably a PEG compound as described herein, or a mixture of two or more different PEG compounds, as described herein.

In one embodiment of the invention, the method of the invention comprises the additional step of dissolving one or more further therapeutic agents in the PEG, such that the pharmaceutical formulation comprises (or consists essentially of) melflufen, or a salt thereof, PEG, and one or more further therapeutic agents as described herein.

In another embodiment of the invention, the method for preparing a pharmaceutical formulation of the invention comprises the step of dissolving melflufen, or a salt thereof, in propylene glycol and PEG. The PEG is preferably a PEG compound as described herein, or a mixture of two or more different PEG compounds, as described herein.

In another embodiment of the invention, the method of the invention comprises the additional step of dissolving one or more further therapeutic agents in the propylene glycol and PEG, such that the pharmaceutical formulation comprises (or consists essentially of) melflufen, or a salt thereof, propylene glycol, PEG, and one or more further therapeutic agents as described herein.

The present invention further provides a method for storing melflufen, or a salt thereof, comprising the steps of preparing a pharmaceutical formulation of the invention and storing the pharmaceutical formulation at a temperature of about −90 to 25° C. Preferably, the pharmaceutical formulation of the invention is stored at a temperature of about 5° C. (for example, 5±3° C., or 5±1° C.) or less, for example 0 to 4° C.

In one embodiment of the invention, the pharmaceutical formulation is stored at about −30 to −10° C., for example −30 to −25, −25 to −15, and −15 to −10° C. Preferably, −25 to −5° C., for example about −20° C. (for example, −20±3° C., or −20±1° C.).

In another embodiment of the invention, the pharmaceutical formulation is stored at about −90 to −60° C., for example −90 to −85, −85 to −75 (for example, about −70° C., for example −70° C.±3° C., or −70° C.±1° C.), −75 to −60° C. Preferably, −85 to −75° C., for example about −80° C. (for example, −80±3° C., or −80±1° C.).

In another embodiment of the invention, the pharmaceutical formulation is stored at about 5 to 25° C., for example about 5 to 12° C., 12 to 18, 18 to 25° C., 20 to 25° C. In particular, 18 to 25° C. or 20 to 25° C., for example about 25° C. (for example, 25±3° C.

Kits

The present invention provides a kit suitable for the preparation of a pharmaceutical formulation according to the invention.

In a preferred embodiment of the invention, the kit of the invention comprises melflufen, or a salt(s) thereof, and propylene glycol.

In another preferred embodiment of the invention, the kit of the invention comprises melflufen, or a salt(s) thereof, and one or more PEG compounds. The one or more PEG compounds is preferably one or more of the PEG compounds described herein.

In one embodiment of the invention, the kit of the invention comprises melflufen, or a salt(s) thereof, propylene glycol and one or more PEG compounds. The one or more PEG compounds is preferably one or more of the PEG compounds described herein.

For the avoidance of doubt the propylene glycol and/or PEG are present in a kit according to the invention in a form and quantity suitable for the preparation of a pharmaceutical formulation according to the invention. The skilled person can readily determine a quantity of propylene glycol and PEG suitable for the preparation of pharmaceutical formulation according to the invention.

In one embodiment of the invention, the kit of the invention additionally comprises one or more further therapeutic agents as described herein.

In another embodiment of the invention, the kit of the invention additionally comprises one or more physiologically acceptable aqueous solvents as described herein.

For the avoidance of doubt, the melflufen, or salt thereof, and optional one or more further therapeutic agents, are present in a kit according to the present invention in a form and quantity suitable for the preparation of a pharmaceutical formulation according to the invention. The skilled person can readily determine a quantity of the melflufen, or a salt thereof, and optional one or more further therapeutic agents, suitable for the use according the present invention.

The following Examples illustrate the invention.

EXAMPLES

Melflufen used in Examples 1, 2 and 3 is the deuterated melflufen compound OPD-5 in its hydrochloride salt form. OPD-5 in its hydrochloride salt form has the following structure:

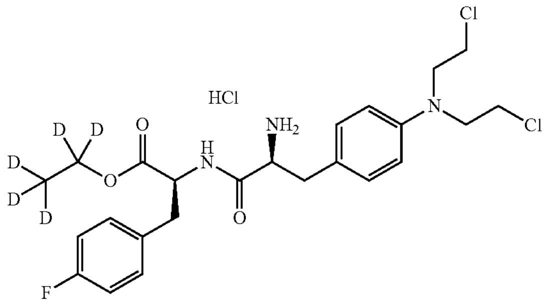 [SMILES: [2H]C([2H])([2H])C([2H])([2H])OC(=O)[C@H](Cc1ccc(F)cc1)NC(=O)[C@@H](N)Cc1ccc(N(CCCl)CCCl)cc1 ; Cl]

Melflufen used in Example 5 is melflufen in one of its following salt forms: hydrochloride, ethanesulfonate, maleate or p-toluenesulfonate. The structures of melflufen in hydrochloride salt form, ethanesulfonate salt form, maleate salt form and p-toluenesulfonate salt form are shown below in Example 4, which provides the synthesis of those salt forms of melflufen.

Example 1: Stability Study of Formulations Containing Melflufen (OPD-5) and Propylene Glycol at 2-8° C., 25° C. and 40° C.

Materials and Methods

Vials (2R type 1 glass vials, Gerresheimer, #35601558) were washed with purified water (≤0.2 µmS/cm, <10 ppb Total Organic Carbon (TOC)). Afterwards, the vials were dried and heat-treated at 300° C. for 2 hours. Rubber stoppers were autoclaved at 121° C. and 2 bar for 15 min.

The formulation was prepared by dissolving melflufen (OPD-5) at a concentration of approximately 20 mg/mL (excluding the mass of the counterion) in propylene glycol (1,2-Propanediol, EMPROVE® exp Ph Eur, BP, USP, Merck Chemicals, #K49954578). 1 mL of the melflufen solution was added into each vial. The filled vials were then closed with a rubber stopper and crimp capped. The 1 mL samples were analysed at $T_0$ (i.e. before storage) and after storage for approximately 4 weeks ($T_1$), 8 weeks ($T_2$), 12 weeks ($T_3$), and 24 weeks ($T_4$) at 2-8° C., 25° C. or 40° C.

RP-HPLC analysis was performed using an Agilent 1100 series Liquid Chromatography, and an)(Bridge® Shield (RP18, 3.5 µm, 4.6×150 mm) column. The method used a 0-80% B gradient over 20 min and a flow of 1.0 mL/min (mobile phase A: 10 mM ammonium acetate pH 5.0/acetonitrile 86/14 v/v; mobile phase B: acetonitrile), a column temperature of 20° C., a sampler temperature of 5° C., and UV detection at 262 nm. The pharmaceutical formulations were diluted to a melflufen concentration of 0.8 mg/mL using an ethanol/acetonitrile diluent (3:7 v/v) prior to RP-HPLC analysis.

Results

The formulation was prepared according to the method described above. Notably, melflufen was found to be readily soluble in propylene glycol. The concentration of melflufen in the formulation was approximately 20 mg/mL.

Figure 2:
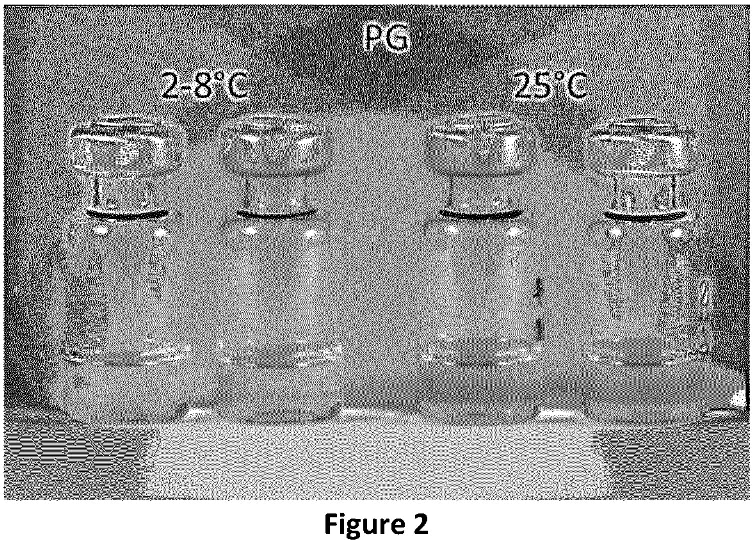
FIGS. 2, 3 and 4 show the visual appearance of the PG formulation following storage at 2-8° C. or 25° C. for 59 days ($T_2$), 98 days ($T_3$) and 168 days ($T_4$), respectively. The samples stored at 2-8° C. have no visible colouration, and the samples stored at 25° C. have a yellow to brown colouration that increases in intensity over time ($T_2$ to $T_4$).
Figure 3:
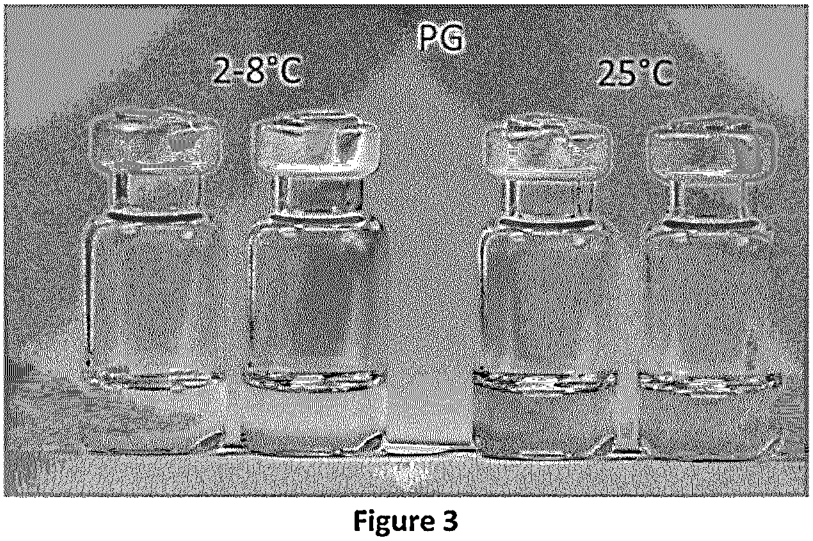
Figure 4:
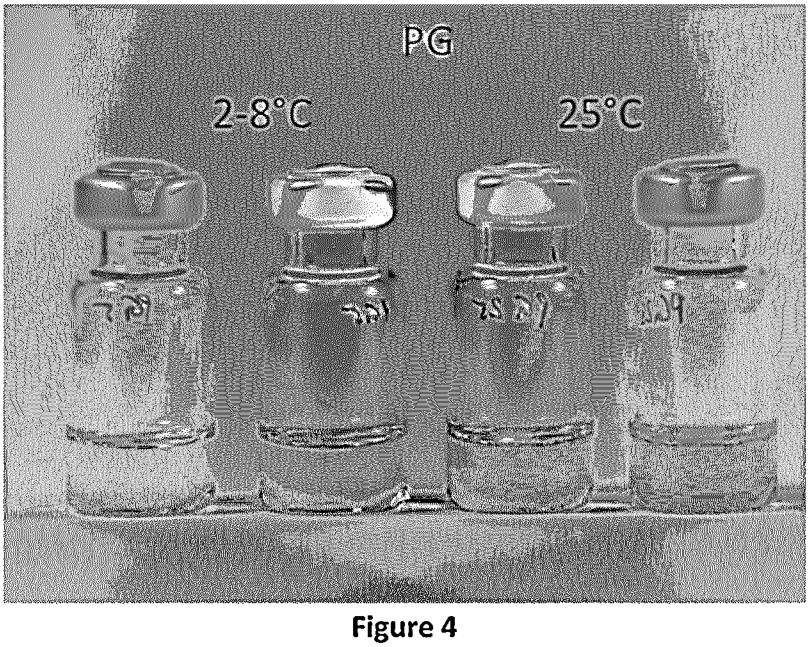

FIG. 1 shows an image of the formulation after storage for approximately 4 weeks ($T_1$ —31 days) at 2-8° C. and 25° C., and under the accelerated storage condition of 40° C. FIG. 2 shows an image of the formulation after storage for approximately 8 weeks ($T_2$ —59 days) at 2-8° C. and 25° C.; FIG. 3 shows an image of the formulation after storage for approximately 12 weeks ($T_3$—98 days) at 2-8° C. and 25° C.; and FIG. 4 shows an image of the formulation after storage for approximately 24 weeks ($T_4$—168 days) at 2-8° C. and 25° C. Notably, at each time point ($T_1$, $T_2$, $T_3$ and $T_4$) the samples stored at 2-8° C. showed no visible colouration. The samples stored at 25° C. and 40° C. displayed a yellow to brown colouration that increased in intensity over time. It is postulated that the coloration is caused by the oxidation of melflufen.

Figure 5:
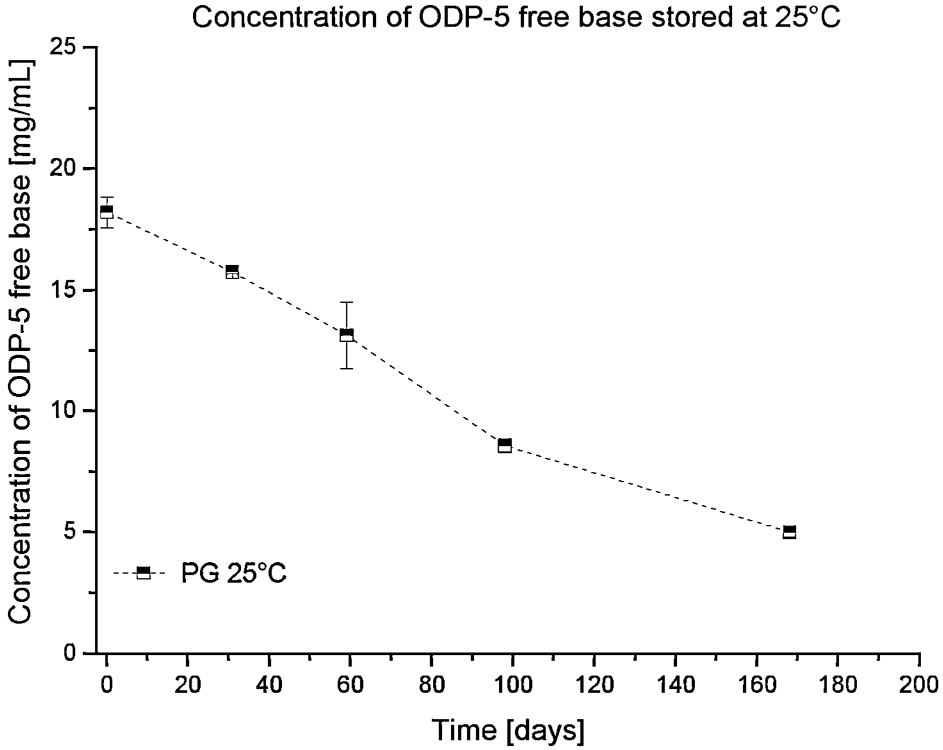
FIGS. 5 and 6 show the change in melflufen (OPD-5) concentration in the PG formulation over time (days) when stored at 25° C. and 2-8° C., respectively.
Figure 6:
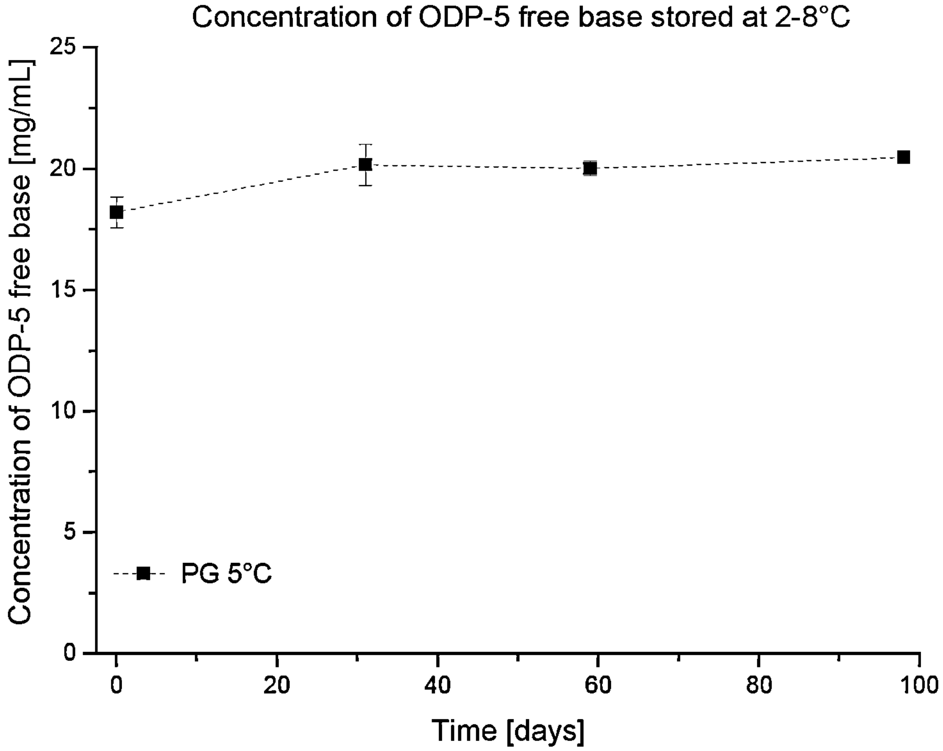

The concentration of melflufen in the formulation was examined by RP-HPLC analysis (Table 1). Before storage (i.e. To) the melflufen concentration of the formulation was approximately 20 mg/mL. For the samples stored at 25° C., the melflufen concentration was observed to decrease over time (Table 1 and FIG. 5). For the samples stored at 2-8° C. no significant change in melflufen concentration was observed (Table 1 and FIG. 6).

TABLE 1

RP-HPLC analysis of melflufen (OPD-5) concentration in the formulation containing melflufen (OPD-5) and propylene glycol.

| Time | | Storage temperature/Concentration of melflufen (ODP-5) [mg/mL] | |
|---|---|---|---|
| point (T) | Sample # | 2-8° C. | 25° C. |
| $T_0$ | 1 | 18.8 | 18.8 |
| | 2 | 17.7 | 17.7 |
| $T_1$ | 1 | 20.1 | 15.7 |
| (31 days) | 2 | 20.2 | 15.8 |
| $T_2$ | 1 | 19.8 | 14.1 |
| (59 days) | 2 | 20.3 | 12.2 |
| $T_3$ | 1 | 20.5 | 8.8 |
| (98 days) | 2 | 20.5 | 8.4 |
| $T_4$ | 1 | 18.4 | 5.1 |
| (168 days) | 2 | 18.3 | 4.9 |

Figure 7:
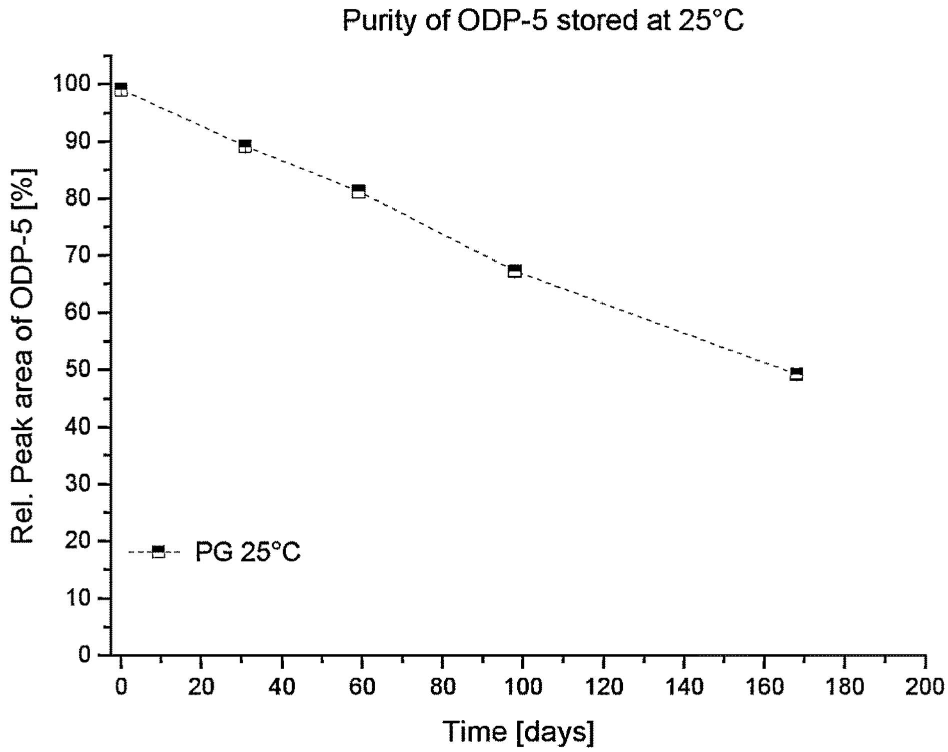
FIGS. 7 and 8 show the change in melflufen (OPD-5) purity in the PG formulation over time (days) when stored at 25° C. and 2-8° C., respectively.
Figure 8:
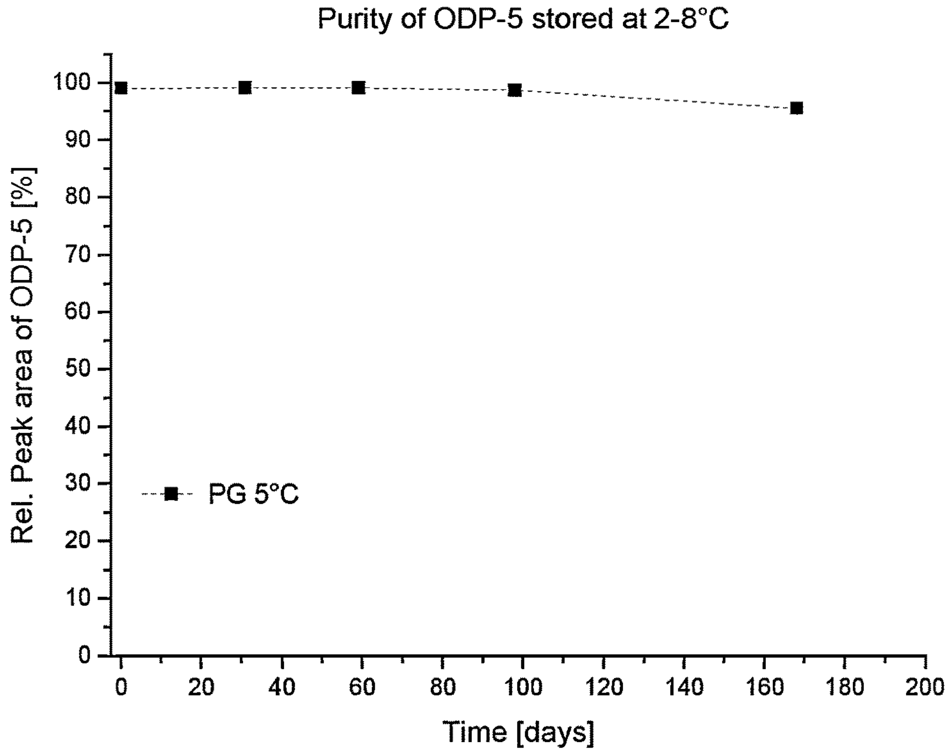

The purity of melflufen (% relative peak area) in the formulation was examined by RP-HPLC analysis (Table 2). Before storage (i.e. To) the melflufen purity of the formulation was approximately 99%. For the samples stored at 25° C., the melflufen purity was observed to decrease over time, with purities of 49.9% (sample #1) and 48.7% (sample #2) observed after storage for 168 days ($T_4$) (Table 2 and FIG. 7). For the samples stored at 2-8° C. only a small decrease in melflufen purity was observed, with purities of 95.4% (sample #1) and 95.8% (sample #2) observed after storage for 168 days ($T_4$) (Table 2 and FIG. 8).

TABLE 2

RP-HPLC analysis of melflufen (OPD-5) purity in the formulation containing melflufen (OPD-5) and propylene glycol.

| Time | | Storage temperature/Purity of melflufen (ODP-5) [% relative peak area] | |
|---|---|---|---|
| point (T) | Sample # | 2-8° C. | 25° C. |
| $T_0$ | 1 | 99.2 | 99.2 |
| | 2 | 99.2 | 99.2 |
| $T_1$ | 1 | 99.1 | 89.0 |
| (31 days) | 2 | 99.3 | 89.3 |
| $T_2$ | 1 | 99.2 | 81.3 |
| (59 days) | 2 | 99.2 | 81.3 |
| $T_3$ | 1 | 99.0 | 68.1 |
| (98 days) | 2 | 98.5 | 66.6 |
| $T_4$ | 1 | 95.4 | 49.9 |
| (168 days) | 2 | 95.8 | 48.7 |

Example 2: Stability Study of Formulations Containing Melflufen (OPD-5) and PEG at 2-8° C., 25° C. and 40° C.

Materials and Methods

Vials (2R type 1 glass vials, Gerresheimer, #35601558) were washed with purified water (≤0.2 µmS/cm, <10 ppb Total Organic Carbon (TOC)). Afterwards, the vials were dried and heat-treated at 300° C. for 2 hours. Rubber stoppers were autoclaved at 121° C. and 2 bar for 15 min.

The formulation was prepared by dissolving melflufen (OPD-5) at a concentration of approximately 20 mg/mL (excluding the mass of the counterion) in polyethylene glycol (polyethylene glycol 300, Emprove exp., Ph. Eur, Merck Chemicals, #K47544702). 1 mL of the melflufen solution was added into each vial. The filled vials were then closed with a rubber stopper and crimp capped. The 1 mL samples were analysed at $T_0$ (i.e. before storage) and after storage for approximately 4 weeks ($T_{1a}$), 8 weeks ($T_{2a}$), 12 weeks ($T_{3a}$), and 24 weeks ($T_{4a}$) at 2-8° C., 25° C. or 40° C.

RP-HPLC analysis was performed using an Agilent 1100 series Liquid Chromatography, and an XBridge® Shield (RP18, 3.5 μm, 4.6×150 mm) column. The method used a 0-80% B gradient over 20 min and a flow of 1.0 mL/min (mobile phase A: 10 mM ammonium acetate pH 5.0/acetonitrile 86/14 v/v; mobile phase B: acetonitrile), a column temperature of 20° C., a sampler temperature of 5° C., and UV detection at 262 nm. The pharmaceutical formulations were diluted to a melflufen concentration of 0.8 mg/mL using an ethanol/acetonitrile diluent (3:7 v/v) prior to RP-HPLC analysis.

Results

The formulation was prepared according to the method described above. Notably, melflufen was found to be readily soluble in PEG 300. The concentration of melflufen in the formulation was approximately 20 mg/mL.

Figure 9:
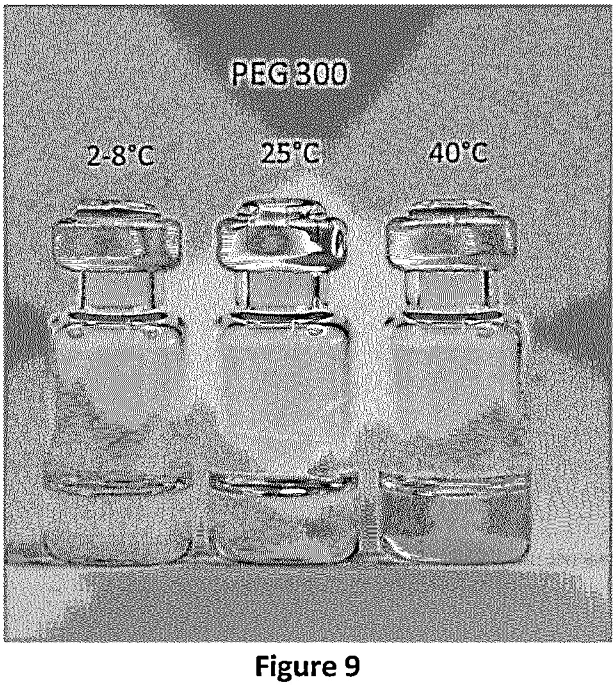
FIG. 9 shows the visual appearance of a pharmaceutical formulation consisting essentially of melflufen (ODP-5) and polyethylene glycol (the "PEG formulation") following storage for 26 days ($T_{1a}$) at 2-8° C., 25° C. or 40° C. The samples stored at 2-8° C. have a slight yellow colouration. The samples stored at 25° C. and 40° C. have a yellow to brown colouration.
Figure 10:
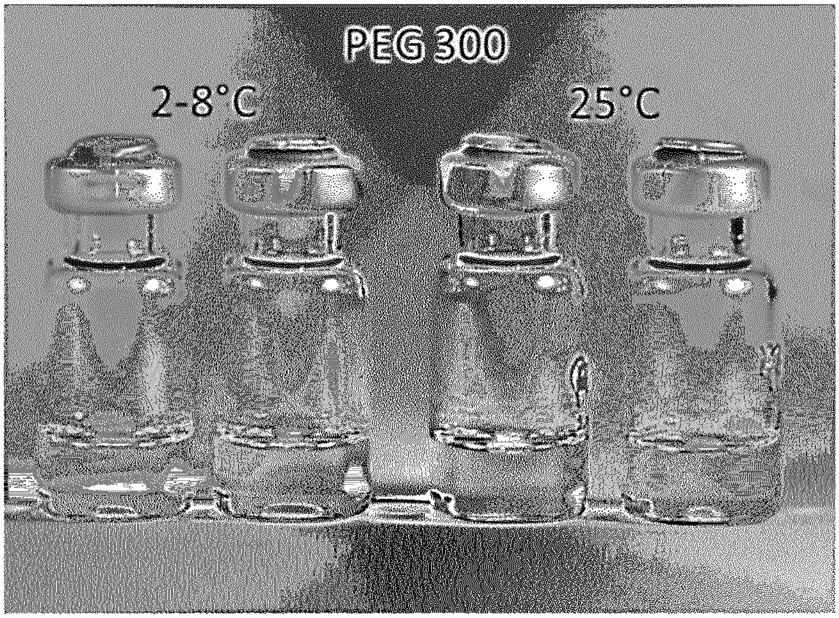
FIGS. 10, 11 and 12 show the visual appearance of the PEG formulation following storage at 2-8° C. or 25° C. for 54 days ($T_{2a}$), 94 days ($T_{3a}$) and 164 days ($T_{4a}$), respectively. The samples stored at 2-8° C. have a slight yellow colouration that increases in intensity over time. The samples stored at 25° C. have a yellow to brown colouration that increases in intensity over time ($T_{2a}$ to $T_{4a}$). At each time point the intensity of the colouration is less for the samples stored at 2-8° C. compared to the samples stored at 25° C.
Figure 11:
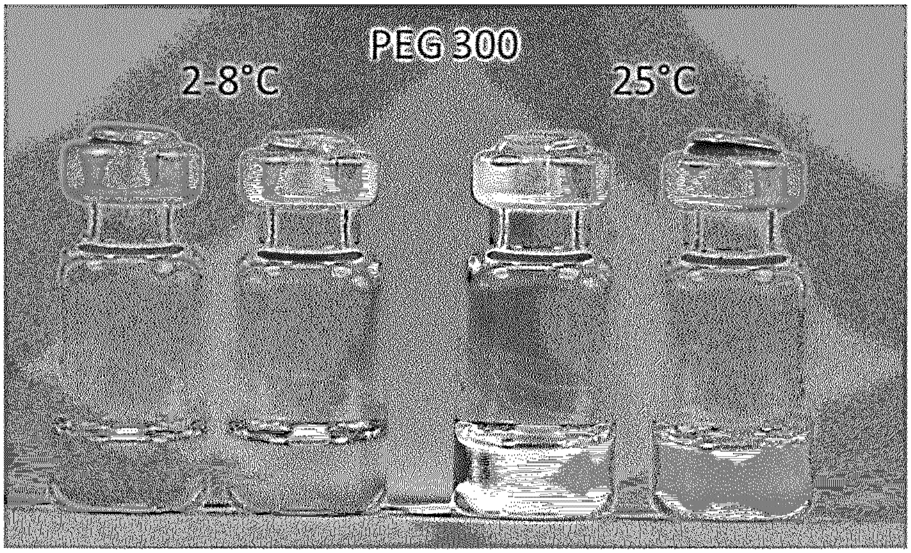
Figure 12:
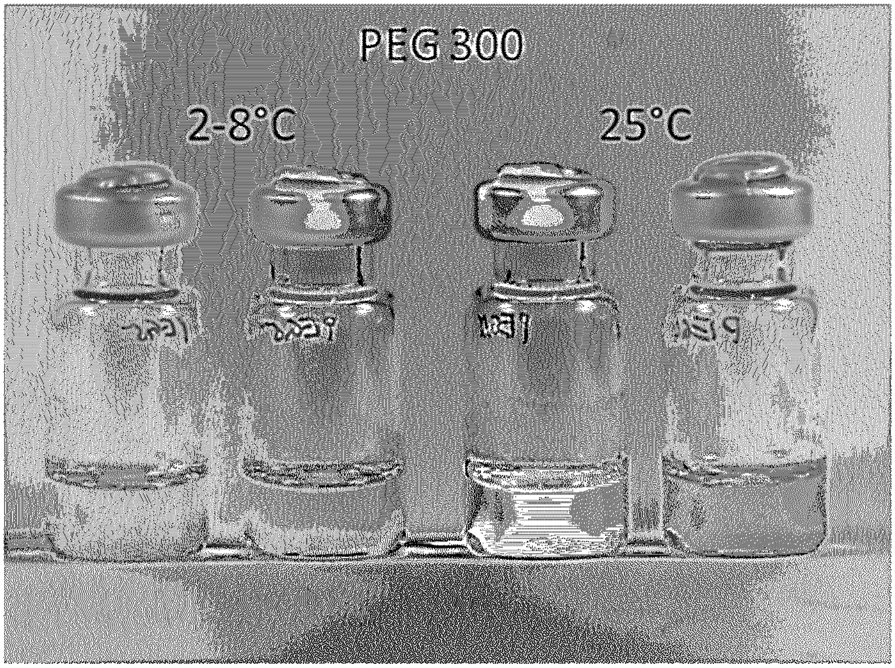

FIG. 9 shows an image of the formulation after storage for approximately 4 weeks ($T_{1a}$—26 days) 2-8° C., 25° C., and under the accelerated storage condition of 40° C. FIG. 10 shows an image of the formulation after storage for approximately 8 weeks ($T_{2a}$—54 days) at 2-8° C. and 25° C.; FIG. 11 shows an image of the formulation after storage for approximately 12 weeks ($T_{3a}$—94 days) at 2-8° C. and 25° C.; and FIG. 12 shows an image of the formulation after storage for approximately 24 weeks ($T_{4a}$—164 days) at 2-8° C. and 25° C. The samples stored at 2-8° C. showed a slight yellow colouration at approximately 4 weeks ($T_{1a}$), and a small increase in the intensity of the yellow colouration was observed over time. The samples stored at 25° C. and 40° C. displayed a yellow to brown colouration that increased in intensity over time. As mentioned above, it is postulated that the coloration is caused by the oxidation of melflufen.

Figure 13:
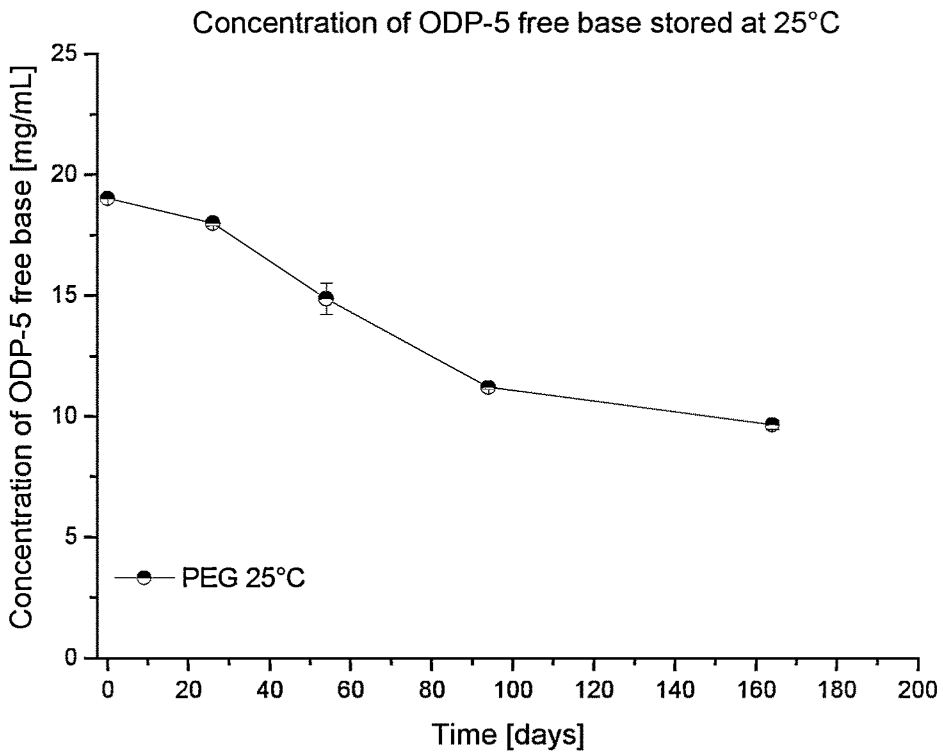
FIGS. 13 and 14 show the change in melflufen (OPD-5) concentration in the PEG formulation over time (days) when stored at 25° C. and 2-8° C., respectively.
Figure 14:
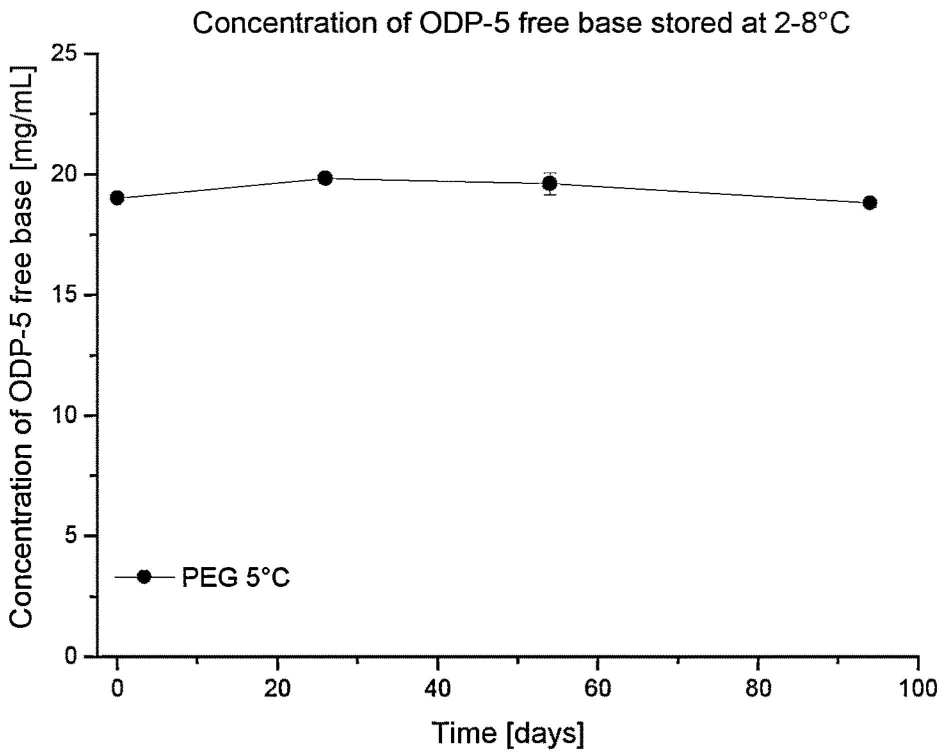

The concentration of melflufen in the formulation was examined by RP-HPLC analysis (Table 3). Before storage (i.e. To) the melflufen concentration of the formulation was approximately 20 mg/mL. For the samples stored at 25° C., the melflufen concentration was observed to decrease over time (Table 3 and FIG. 13). For the samples stored at 2-8° C. no significant change in melflufen concentration was observed (Table 3 and FIG. 14).

TABLE 3

RP-HPLC analysis of melflufen (OPD-5) purity in the formulation containing melflufen (OPD-5) and PEG.

| Time point (T) | Sample # | Storage temperature/Concentration of melfufen (ODP-5) [mg/mL] 2-8° C. | 25° C. |
|---|---|---|---|
| $T_0$ | 1 | 19.0 | 19.0 |
| | 2 | 19.1 | 19.1 |
| $T_{1a}$ | 1 | 19.9 | 18.1 |
| (26 days) | 2 | 19.8 | 17.9 |
| $T_{2a}$ | 1 | 19.9 | 14.4 |
| (54 days) | 2 | 19.3 | 15.3 |
| $T_{3a}$ | 1 | 18.7 | 11.2 |
| (94 days) | 2 | 18.9 | 11.3 |
| $T_{4a}$ | 1 | 18.7 | 9.8 |
| (164 days) | 2 | 18.7 | 9.5 |

Figure 15:
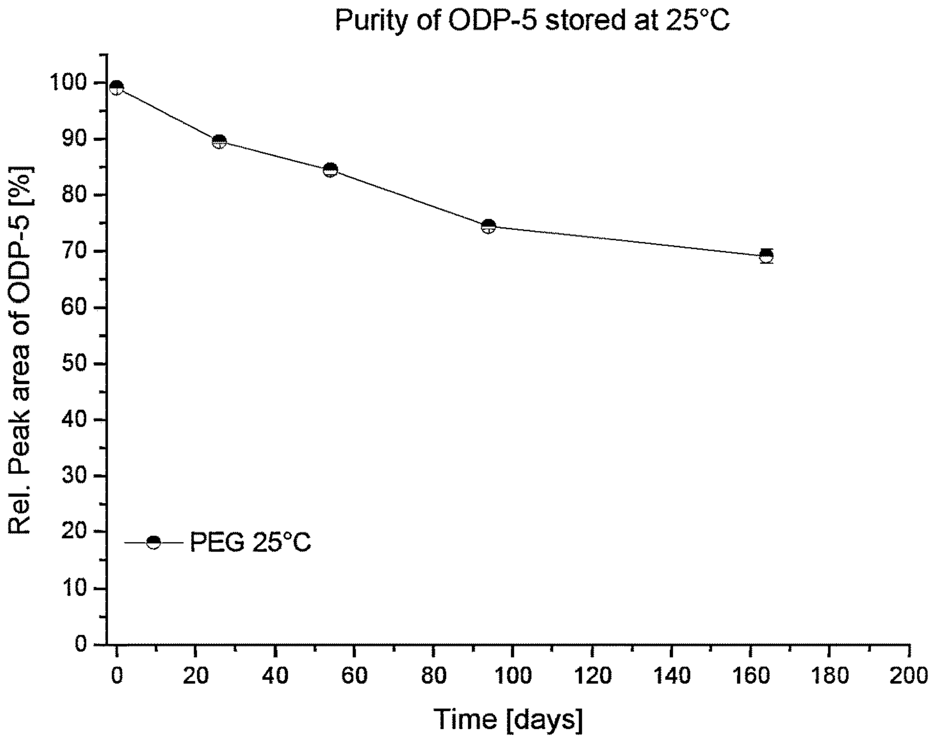
FIGS. 15 and 16 show the change in melflufen (OPD-5) purity in the PEG formulation over time (days) when stored at 25° C. and 2-8° C., respectively.
Figure 16:
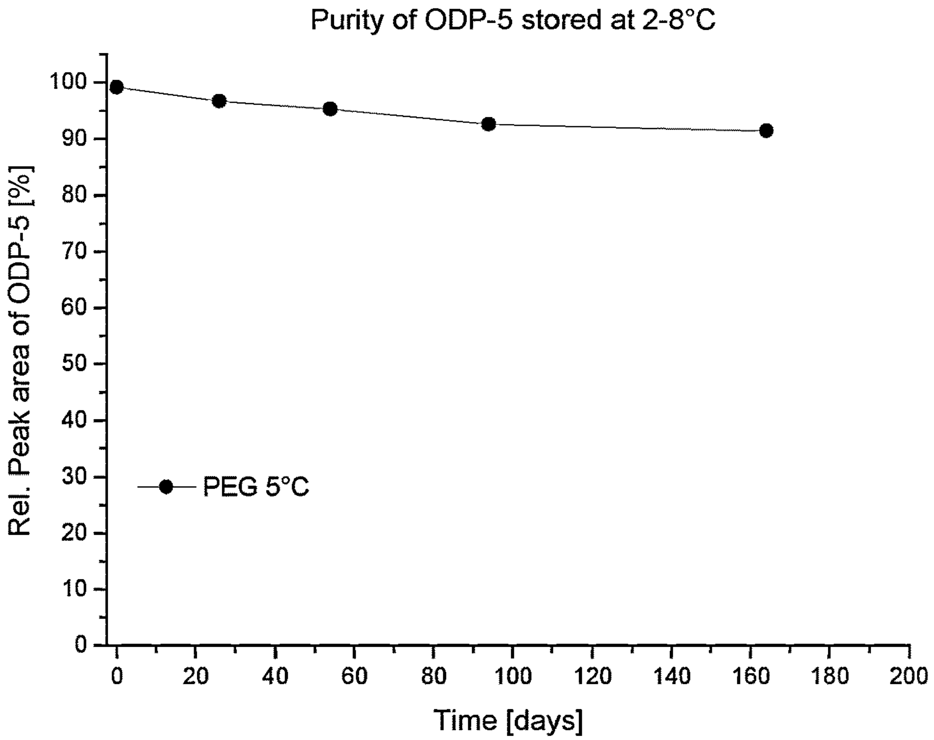

The purity of melflufen (% relative peak area) in the formulation was examined by RP-HPLC analysis (Table 4). Before storage (i.e. To) the melflufen purity (% relative peak area) of the formulation was approximately 99%. For the samples stored at 25° C., the melflufen purity (% relative peak area) was observed to decrease over time, with purities of 70% (sample #1) and 68.1% (sample #2) observed after storage for 164 days ($T_{4a}$) (Table 4 and FIG. 15). For the samples stored at 2-8° C. only a small decrease in melflufen purity was observed, with purities of 91.4% (sample #1) and 91.3% (sample #2) observed after storage for 164 days ($T_{4a}$) (Table 4 and FIG. 16).

TABLE 4

RP-HPLC analysis of melflufen (OPD-5) purity in the formulation containing melflufen (OPD-5) and PEG.

| Time point (T) | Sample # | Storage temperature/Purity of melfufen (ODP-5) [% relative peak area] 2-8° C. | 25° C. |
|---|---|---|---|
| $T_0$ | 1 | 99.2 | 99.2 |
| | 2 | 99.2 | 99.2 |
| $T_{1a}$ | 1 | 96.7 | 89.3 |
| (26 days) | 2 | 96.9 | 89.6 |
| $T_{2a}$ | 1 | 95.2 | 83.8 |
| (54 days) | 2 | 95.5 | 85.1 |
| $T_{3a}$ | 1 | 92.7 | 74.2 |
| (94 days) | 2 | 92.6 | 74.7 |
| $T_{4a}$ | 1 | 91.4 | 70.0 |
| (164 days) | 2 | 91.3 | 68.1 |

Example 3: Stability Study of Formulations Containing Melflufen (OPD-5) and Propylene Glycol at −20° C. and −70° C.

Materials and Methods 536.25 mg of melflufen (OPD-5) was weighed into a 20 mL volumetric flask. The flask was then filled with propylene glycol (W294004-1 Kg-K, Lot no: MKCD8681, Sigma-Aldrich). The resulting mixture was vortexed for 3 minutes. The mixture was then stirred for 15 minutes at 28° C. with occasional vortexing to furnish a clear solution having a melflufen concentration of approximately 20 mg/mL (excluding the mass of the counterion). The solution was aliquoted into 1 mL vials and stored at −70° C. or at −20° C.

The concentration and purity (% relative peak area) of melflufen in the propylene glycol formulation was analysed at time 0 ($T_{0b}$) and then every 1 month by RP-HPLC. For each time point, two replicated were analysed (i.e. two separate vials of the formulation). At each time point the vials were visually checked for any color change or precipitation.

RP-HPLC analysis was performed using an Agilent 1100 series Liquid Chromatography, and an XBridge® C18 (2.1×100 mm, 3.5 μm) column. The method used a 5-95% B gradient over 6 min and a flow of 0.8 mL/min (mobile phase A: 0.1% formic acid in water; mobile phase B: 0.1% formic acid in acetonitrile), a column temperature of 55° C., a sampler temperature of 25° C., and UV detection at 262 nm. Samples were then diluted to 200 μg/mL concentration in DMA before injection into RP-HPLC. An injection volume of 5 μL was used.

Results

Figure 17:
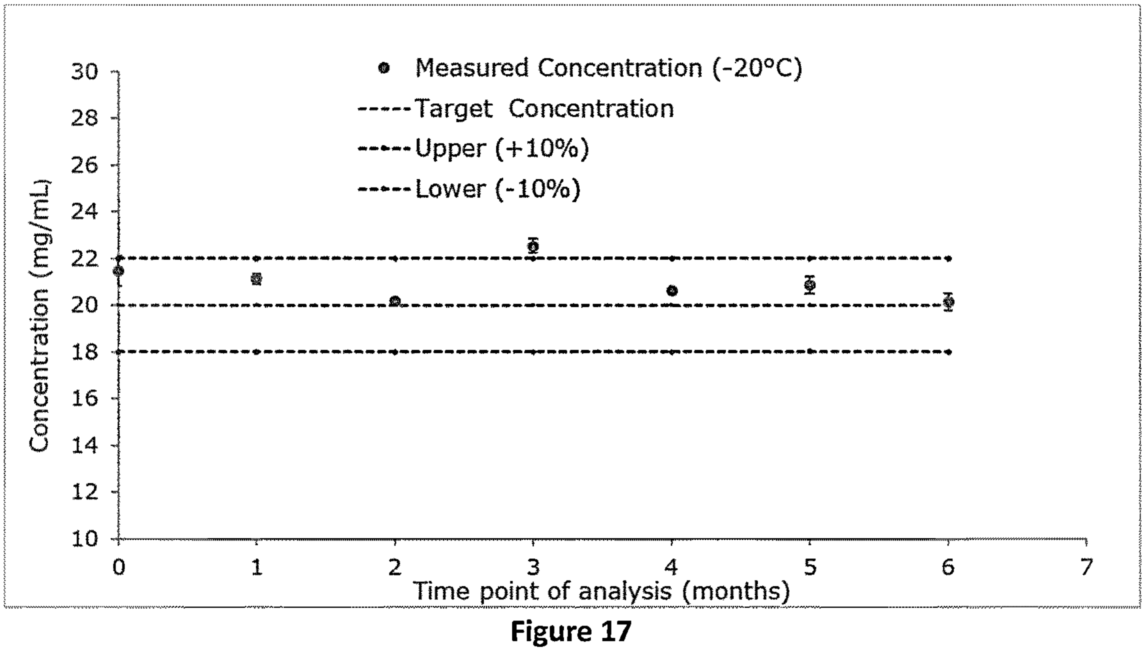
FIGS. 17 and 18 show the change in melflufen (OPD-5) concentration in the PG formulation over time (months) when stored at −20° C. and at −70° C., respectively. Error bar represents the standard deviation of 2 replicates. Central dashed line represents the target concentration of melflufen in the form of OPD-5 (approximately 20 mg/mL, excluding mass of the counterion). Upper and lower dashed lines represent +10% and −10% of the target concentration, respectively.
Figure 18:
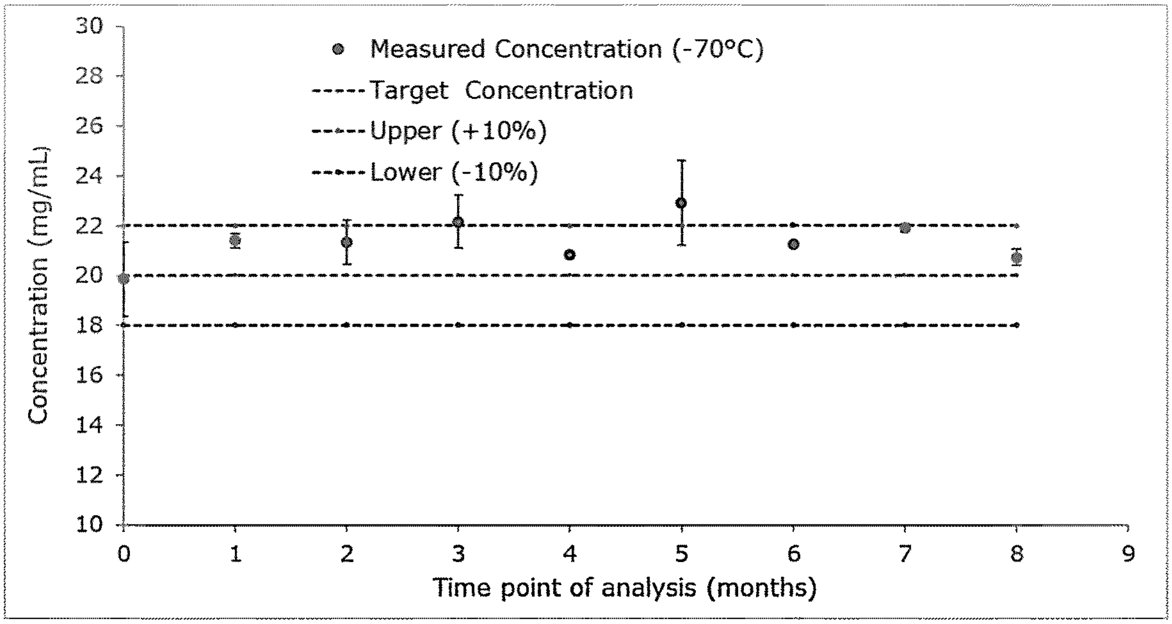

The stability of the hydrochloride salt of melflufen (OPD-5) in propylene glycol (PG) solution at −70° C. and at −20° C. was investigated. No colour change or precipitation was observed in any of the samples over 6-8 month test period. As shown in FIG. 17, melflufen (OPD-5) in the propylene glycol formulation was stable at −20° C. for at least 6 months, with no notable change in melflufen (OPD-5) concentration over the 6 month test period. As shown in FIG. 18, melflufen (OPD-5) in the propylene glycol formulation was stable at −70° C. for at least 6 months, with no notable change in melflufen (OPD-5) concentration over the 8 month test period. Melflufen (OPD-5) was found to retain a melflufen purity of greater than 99.5% (relative to the melflufen purity before storage of the formulation) when stored at −20° C. for 6 months and when stored at −70° C. for 8 months.

Example 4: Preparation of Melflufen Salts

The hydrochloride salt of melflufen may be prepared as disclosed in WO 01/96367, which is incorporated herein by reference. Ethanesulfonate, maleate and p-toluenesulfonate salts of melflufen were prepared by treating the melflufen freebase with 1 equivalent of the respective acid in dichloromethane or ethyl acetate. If required, heptane was added to initiate salt precipitation. All salts were isolated as white solids in a 1:1 ratio of melflufen and counterion, and dried under high vacuum. Melflufen freebase was prepared from melflufen hydrochloride using $NaHCO_3$ and dichloromethane (DCM). Melflufen hydrochloride was suspended in 100 mL of dichloromethane before an ice-cold solution of $NaHCO_3$(aq) was added. The mixture was shaken for 30 seconds and the phases were allowed to settle. The organic phase was collected and dried over $MgSO_4$ before the solvent was removed in vacuo at 0° C. Melflufen freebase was isolated as a colorless oil. No degradation of melflufen was observed by HPLC analysis and the oil was stable at room temperature for several days.

4.1: Preparation of melflufen ethanesulfonic acid salt (ethanesulfonic acid;ethyl (2S)-2-[[(2S)-2-amino-3-[4-[bis(2-chloroethyl)amino]phenyl]propanoyl]amino]-3-(4-fluorophenyl)propanoate)

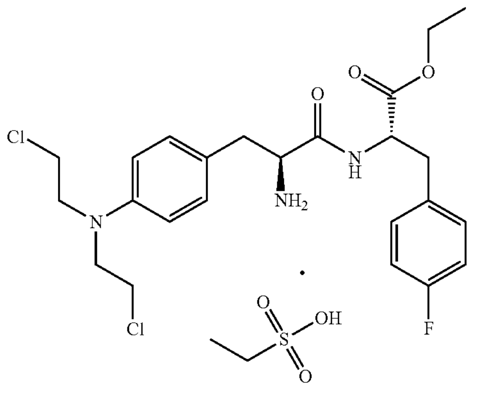

Melflufen freebase (120 mg, 0.24 mmol) was dissolved in DCM (1 mL) and ethansulfonic acid (26.4 mg, 0.24 mmol) in DCM (200 μL) was added. Heptane (500 μL) was added and the mixture was stirred for 10 minutes before being concentrated in vacuo to furnish a white solid. The white solid was triturated with heptane (1 mL) and dried in vacuo to give the title compound as a white solid. Yield 97 mg (66%). NMR reveals salt formation of 1:1 (mol). $^1$H NMR (400 MHz, DMSO-d6) δ 8.94 (d, J=7.6 Hz, 1H), 8.12-7.95 (m, 2H), 7.35-7.21 (m, 2H), 7.19-7.04 (m, 4H), 6.77-6.64 (m, 2H), 4.61-4.51 (m, 1H), 4.07 (q, J=7.1 Hz, 2H), 3.93 (s, 1H), 3.71 (s, 8H), 3.14-2.92 (m, 3H), 2.80 (dd, J=14.3, 8.2 Hz, 1H), 2.38 (q, J=7.4 Hz, 2H), 1.13 (t, J=7.1 Hz, 3H), 1.06 (t, J=7.4 Hz, 3H).

4.2: Preparation of melflufen maleic acid salt (Ethyl (2S)-2-[[(2S)-2-amino-3-[4-[bis(2-chloroethyl)amino]phenyl]propanoyl]amino]-3-(4-fluorophenyl)propanoate;maleic acid)

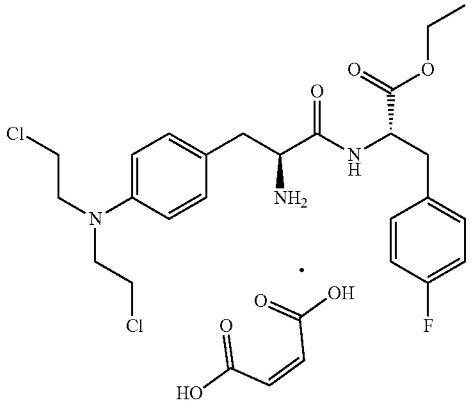 [SMILES: CCOC(=O)[C@H](Cc1ccc(F)cc1)NC(=O)[C@@H](N)Cc1ccc(N(CCCl)CCCl)cc1 ; O=C(O)/C=C\C(=O)O]

Melflufen freebase (108 mg, 0.22 mmol) was dissolved in 1080 μL EtOAc and maleic acid (25 mg, 0.22 mmol) was added portion-wise while stirring. After 5-10 minutes a heavy precipitate formed and the mixture was diluted with 1 mL EtOAc and stirred for additional 30 minutes. The precipitate was collected by suction filtration and washed with 300 μL of EtOAc and dried in vacuo. Yield 104 mg (78%). HPLC purity 95%. MS m/z 498$[M+H]^+$. NMR reveals salt formation 1:1. $^1$H NMR (400 MHz, DMSO-d6) δ 8.92 (d, J=7.7 Hz, 1H), 7.97 (s, 3H), 7.35-7.22 (m, 2H), 7.18-7.05 (m, 4H), 6.78-6.65 (m, 2H), 6.02 (s, 2H), 4.55 (td, J=8.0, 6.2 Hz, 1H), 4.12-4.05 (m, 2H), 3.92 (dd, J=8.4, 5.0 Hz, 1H), 3.71 (s, 8H), 3.11-2.93 (m, 3H), 2.78 (dd, J=14.3, 8.4 Hz, 1H), 1.13 (t, J=7.1 Hz, 3H).

4.3: Preparation of melflufen p-toluenesulfonic acid salt (Ethyl (2S)-2-[[(2S)-2-amino-3-[4-[bis(2-chloroethyl)amino]phenyl]propanoyl]amino]-3-(4-fluorophenyl)propanoate;4-methylbenzenesulfonic acid)

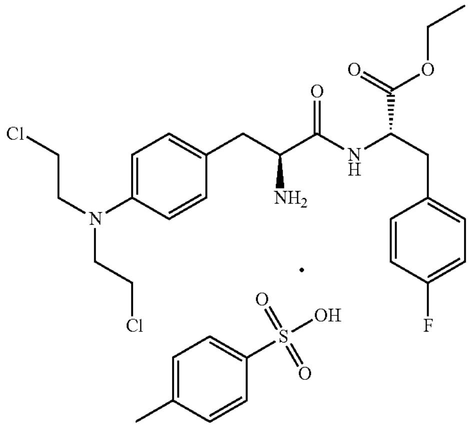

Melflufen freebase (100.8 mg, 0.20 mmol) was dissolved in 1008 μL EtOAc and p-toluenesulfonic acid monohydrate (41 mg, 0.20 mmol) in EtOAc (850 μL) was added. After 5-10 minutes a heavy precipitate formed, and the mixture was diluted with 2 mL EtOAc and stirred for 1 hour. The precipitate was collected by suction. The precipitate was washed with EtOAc (500 μL) and dried in vacuo to give 65 mg (48%) of the title compound as a white solid HPLC purity 95%. MS m/z 498[M+H]t NMR reveals salt formation of 1:1. $^1$H NMR (400 MHz, DMSO-d6) δ 8.94 (d, J=7.6 Hz, 1H), 8.10-7.95 (m, 3H), 7.55-7.44 (m, 2H), 7.33-7.24 (m, 2H), 7.19-7.06 (m, 6H), 6.76-6.65 (m, 2H), 4.55 (td, J=8.0, 6.2 Hz, 1H), 4.07 (q, J=7.1 Hz, 2H), 3.94 (s, 1H), 3.71 (s, 8H), 3.11-2.92 (m, 3H), 2.79 (dd, J=14.3, 8.3 Hz, 1H), 2.29 (s, 3H), 1.13 (t, J=7.1 Hz, 3H)

Example 5: Solubility and Stability Study of Liquid Formulations Containing a Melflufen Salt and Propylene Glycol

Materials and Methods

The solubility and stability of ethanesulfonic acid, p-toluenesulfonic acid and hydrochloric acid salts of melflufen in propylene glycol were investigated. 10 mg of each melflufen salt was transferred to transparent 4 mL vials and propylene glycol (Merck Lot # K51750378936, 1.07478.2500) was added to a concentration of 20 mg/mL. The vials were shaken for a short time and stored at room temperature (RT, 20-25° C.).

The stability of the melflufen salt solutions were analysed at weekly time points by Analytical HPLC-MS using an Agilent 1100 series Liquid Chromatograph/Mass Selective Detector (MSD) (Single Quadrupole) equipped with an electrospray interface and a UV diode array detector. Analysis was performed by using an ACE 3 C8 (3.0×50 mm) column with a gradient of 10-97% acetonitrile in 0.1% aqueous TFA over 3 min and a flow of 1 mL/min. UV was monitored at 305 nm. At each time point (0, 1, 2, 3, 4, 5, 6 and 7 weeks) 10 μL of the melflufen solution was diluted with 490 μL of acetonitrile before HPLC-MS analysis.

The solubility and stability of maleic acid salt of melflufen is investigated using the same protocol as described above for the ethanesulfonic acid, p-toluenesulfonic acid and hydrochloric acid salts of melflufen.

Results

The formulations were prepared using the method described above. Each of the melflufen salts were found to have good solubility in propylene glycol, with a solution of 20 mg/mL of melflufen being easily prepared.

TABLE 5

RP-HPLC analysis of melflufen purity in the liquid formulation containing a melflufen salt and propylene glycol.

| Time | Purity of melfufen [% relative peak area] in the liquid formulation containing a melfufen salt and propylene glycol at RT. | | |
|---|---|---|---|
| point (weeks) | ethanesulfonic acid | p-toluenesulfonic acid | hydrochloric acid salt |
| 0 | 100 | 100 | 100 |
| 1 | 95 | 96 | 100 |
| 2 | 94 | 95 | 95 |
| 3 | 93 | 93 | 94 |

TABLE 5-continued

RP-HPLC analysis of melflufen purity in the liquid formulation containing a melflufen salt and propylene glycol.

| Time | Purity of melfufen [% relative peak area] in the liquid formulation containing a melfufen salt and propylene glycol at RT. | | |
|---|---|---|---|
| point (weeks) | ethanesulfonic acid | p-toluenesulfonic acid | hydrochloric acid salt |
| 4 | 94 | 91 | 92 |
| 5 | 89 | 89 | 89 |
| 6 | 88 | 88 | 87 |
| 7 | 87 | 87 | 85 |

Each of the ethanesulfonic, p-toluenesulfonic, and hydrochloric acid salts of melflufen were found to have good stability over 7 weeks when stored at room temperature (RT). Each of the solutions were found to have a melflufen purity of over 90% after 4 weeks of storage at RT and at least 85% after 7 weeks of storage at RT. For each solution the main degradation product was an N-monodesalkyl aniline product, which has the following structure:

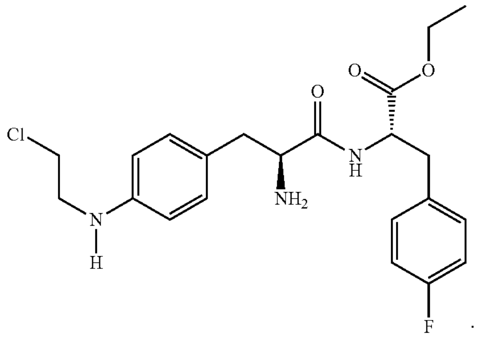 [SMILES: CCOC(=O)[C@H](Cc1ccc(F)cc1)NC(=O)[C@@H](N)Cc1ccc(NCCCl)cc1]

For the melflufen hydrochloride salt solution, a trace (i.e. less than 0.5% relative peak area) amount of an N-bis-dealkylated degradation product was detected after 7 weeks storage at RT. The N-bis-dealkylated degradation product has the following structure:

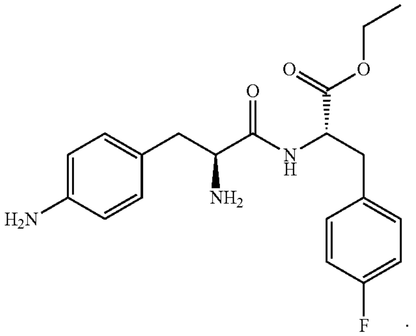 [SMILES: CCOC(=O)[C@H](Cc1ccc(F)cc1)NC(=O)[C@@H](N)Cc1ccc(N)cc1]

Example 6: Kg Scale Synthesis of OPD5

OPD-5 can be synthesised, for example on a kg scale, using the following method:

Step (i): Production of ($^2H_5$)ethyl(2S)-2-amino-3-(4-fluorophenyl)propanoate hydrochloride by esterification of p-fluoro-L-phenylalanine with Ethanol ($d_6$)

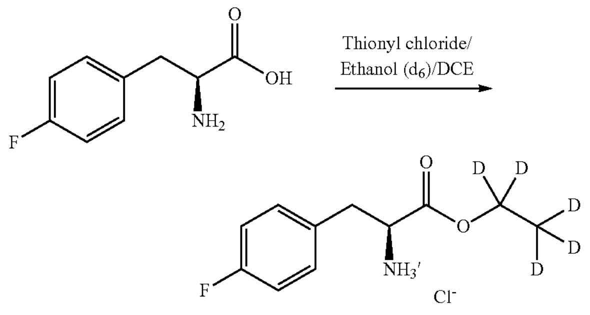

p-Fluoro-L-phenylalanine (1.0 kg, CAS Number 1132-68-9) was slurried in a mixture of ethanol-d6 (2.5 L, CAS Number: 1516-08-1) and 1,2-dichloroethane (2.0 L). A scrubber containing NaOH (5 M solution) was connected to the outlet of the reactor, after the condenser. In order to follow the degradation of the scrubber fluid, bromothymol blue (1-2 mg) was added.

The reactor was heated to an inner temperature of 60° C. When the inner temperature reached 60° C., addition of thionyl chloride (600 mL) at a slow rate was started. Initially a very thick precipitate was formed. The initially very thick slurry thinned during the course of the reaction. Total time for the addition was ca. 3 h. The inner temperature was allowed to reach a maximum of 70° C. and was controlled by adjusting the mantel temperature accordingly. After full addition the mantel temperature was adjusted to keep the inner temperature between 65-70° C.

Full conversion to the desired ($^2H_5$)ethyl(2S)-2-amino-3-(4-fluorophenyl)propanoate hydrochloride was achieved after 3 h after point of complete addition of the thionyl chloride. After full conversion was confirmed (LC-MS analysis with conditions as follows: ACE 3 C8 (3.0×50 mm) column, with a 10-90% B gradient over 3 min; Mobile phase A, water 0.1% TFA, mobile phase B, pure acetonitrile, flow of 1 mL/min, UV detection at 215-395, 254 and 220 nm), the reaction was cooled (inner temperature ca. 45° C.) and tert-butyl methyl ether (12.5 L) was added giving the product as a white precipitate. The mixture was stirred in order to get a homogeneous mixture.

The mixture was then cooled to an inner temperature of 0° C. and matured at this temperature for ca. 30 min before filtration. The solid ($^2H_5$)ethyl(2S)-2-amino-3-(4-fluorophenyl)propanoate hydrochloride was washed with ca. 1 L of tert-butyl methyl ether and then dried at a maximum temperature of 30° C. under reduced pressure. The product was sieved carefully in order to remove lumps, if present. Isolated yield of ($^2H_5$)ethyl(2S)-2-amino-3-(4-fluorophenyl) propanoate hydrochloride was 92%. LC-MS: $t_R$ 1.43 min, m/z [M+H] 217.

Step (ii): Kg scale production of ($^2H_5$)ethyl (2S)-2-[(2S)-3-{4-[bis(2-chloroethyl)amino]phenyl}-2-{[tert-butoxy)carbonyl]-amino}propanamido]-3-(4-fluorophenyl)propanoate

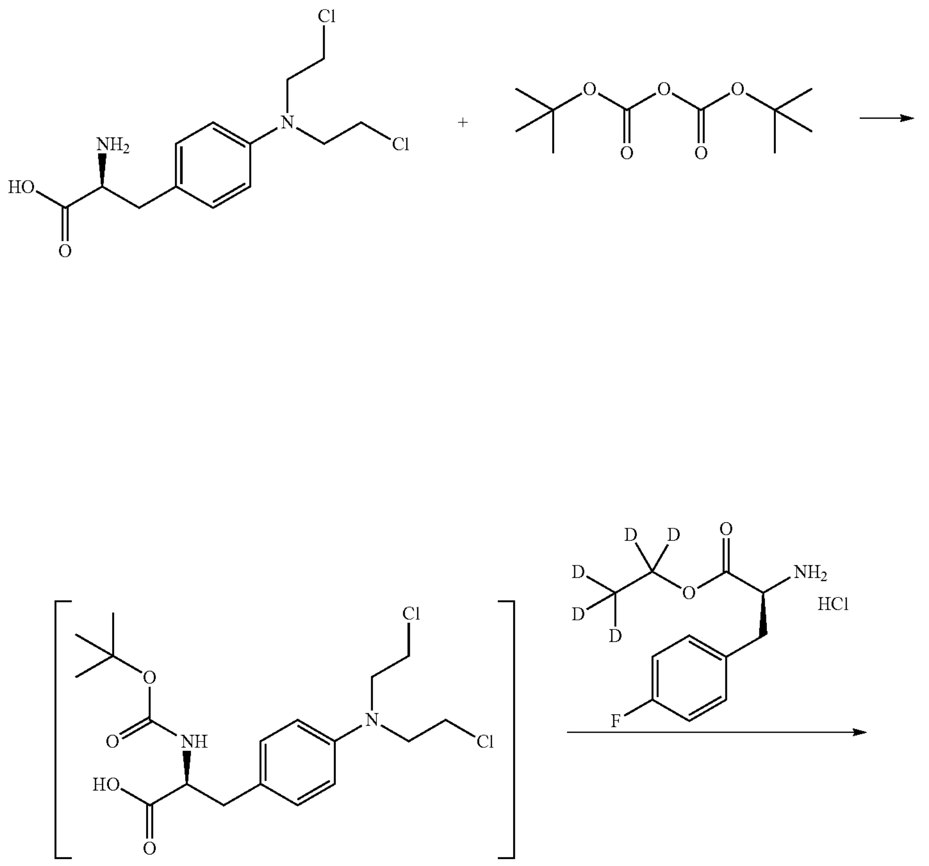

-continued

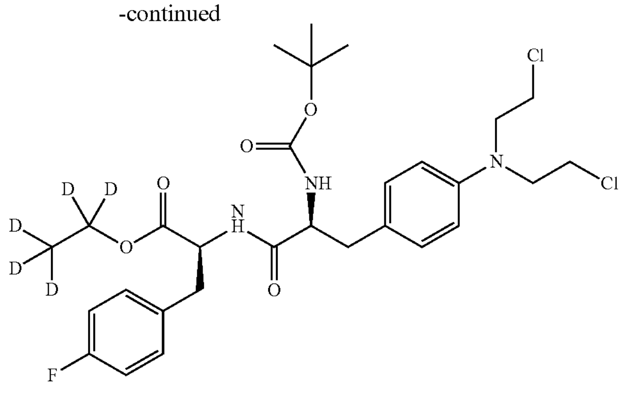

Melphalan (1.663 kg, 5.45 mol, 1 eq.) was added to a mixture of purified water (16.0 kg), NaOH (32%, aq., 1.04 kg) and tetrahydrofuran (10.0 kg) at 10-15° C. A mixture of di-tert-butyl dicarbonate (1.308 kg, 5.99 mol, 1.1 eq.) and tetrahydrofuran (4.75 kg) was added at 10-15° C. The reaction mixture was stirred for 4-5 h at 18-23° C. until minimum 97.0% (HPLC) conversion of Melphalan into was achieved. The temperature was adjusted to 15-20° C., and while keeping this temperature, pH was adjusted to 2.5-3.0 with 1.5 M HCl. Ethyl acetate (7.34 kg) was added, and the phases were separated. The aqueous phase was extracted with ethyl acetate (7.34 kg). The combined organic phases were dried with magnesium sulfate, filtered, and the filter cake was washed with ethyl acetate. The solvents were removed by distillation in vacuo and the residue containing (2S)-3-{4-[bis(2-chloroethyl)amino]phenyl}-2-{[(tert-butoxy)carbonyl]-amino}propanoic acid was dried in vacuo for minimum 12 h at 20-25° C. HPLC: retention time 11.9 min. (HPLC conditions were as follows: sample solvent acetonitrile:water, 1:1 (v/v), Waters, Atlantic $T_3$ (3μ, 4.6× 150 mm) column, 10-90-10% B gradient over 23 min, flow of 1 mL/min, mobile phase A: 500 phosphoric acid 85% in 1.0 L MQ-water, mobile phase B: 500 μL phosphoric acid 85% in 1.0 acetonitrile, with UV detection at 262 nm).

The (2S)-3-{4-[bis(2-chloroethyl)amino]phenyl}-2-{[(tert-butoxy)carbonyl]-amino}propanoic acid residue was redissolved in dichloromethane (44.0 kg). 4-Methylmorpholine (1.378 kg, 13.63 mol, 2.5 eq.) was added, followed by ($^2H_5$)ethyl(2S)-2-amino-3-(4-fluorophenyl)propanoate hydrochloride (1.377 kg, 5.45 mol, 1.0 eq.), 1-hydroxybenzotriazole, $H_2O$ (0.083 kg, 0.54 mol, 0.1 eq.) and N-(3-dimethylaminopropyl)-N'-ethylcarbodiimide, HCl (1.045 kg, 5.45 mol, 1.0 eq.). The reaction mixture was stirred for 3-4 h at 18-23° C., until minimum 97.0% (HPLC) conversion of (2S)-3-{4-[bis(2-chloroethyl)amino]phenyl}-2-{[(tert-butoxy)carbonyl]-amino}propanoic acid into ($^2H_5$) ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate was achieved (HPLC conditions were as follows: sample solvent acetonitrile, Waters, Atlantic $T_3$ (3μ, 4.6×150 mm) column, 10-90-10% B gradient over 23 min, flow of 1 mL/min, mobile phase A: 500 μL phosphoric acid 85% in 1.0 L MQ-water, mobile phase B: 500 μL phosphoric acid 85% in 1.0 acetonitrile, with UV detection at 262 nm.).

The pH was adjusted to 3.0-4.0 with 5% $KHSO_4$ (aq.). The organic phase was secured and the aqueous phase was extracted with dichloromethane (29.0 kg). The first organic phase was washed with 6% $NaHCO_3$. The organic phase was secured and the remaining aqueous phase was back-extracted with the second organic phase. The combined organic phases were dried with magnesium sulfate, filtered, and washed with dichloromethane. The dried organic phase was concentrated by distillation in vacuo to 22-26 L. The reduced organic phase was applied to column chromatography (silica gel (40-63 pm, 22.4 kg), n-heptane (6.7 kg) and dichloromethane (52.2 kg)). The column was eluted with 6% ethyl acetate/dichloromethane. The fractions containing ($^2H_5$)ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate (TLC) were combined and evaporated under reduced pressure to 26-28 L. Ethyl acetate (5.8 kg) was added, and the evaporation was continued to 26-28 L. This procedure was repeated. After addition of ethyl acetate precipitation of ($^2H_5$)ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate started. Optionally, seed crystals of ($^2H_5$)ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate may be added to assist the precipitation. Ethyl acetate (5.8 kg) was added again, and the optional seeding step may be repeated. The mixture was evaporated under reduced pressure to 19-21 L and n-heptane (22.1 kg) was added at 35-45° C. The suspension was cooled to −2 to 2° C. and stirred for 2-18 h. The solid was isolated by centrifugation, and the filter cake was washed with n-heptane. The solid was dried in vacuo at 30° C. to give ($^2H_5$)ethyl (2S)-2-[(25)-3-{4-[bis(2-chloroethyl)amino]phenyl}-2-{[(tert-butoxy)carbonyl]-amino}propanamido]-3-(4-fluorophenyl)propanoate (2.6 kg, 80%) as a white to slightly yellow solid material. HPLC: retention time 13.4 min.

Step (iii): Kg scale production of OPD5 in its HCl salt form ($^2H_5$)ethyl (2S)-2-[(2S)-2-amino-3-{4-[bis(2-chloroethyl)amino]phenyl}propanamido]-3-(4-fluorophenyl)propanoate hydrochloride)

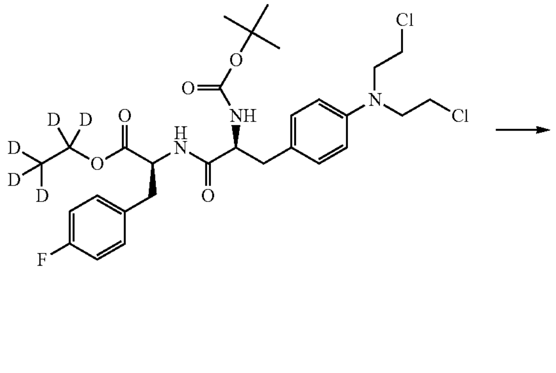

-continued

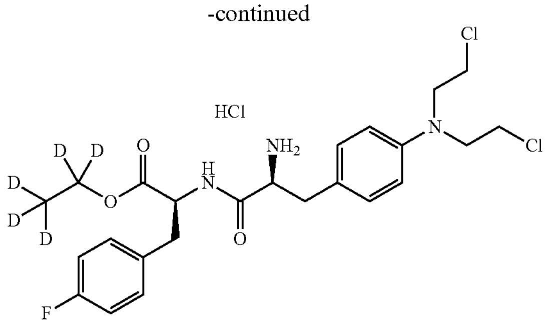

A solution of ($^2H_5$)ethyl (25)-2-[(25)-3-{4-[bis(2-chloroethyl)amino]phenyl}-2-{[(tert-butoxy)carbonyl]-amino}propanamido]-3-(4-fluorophenyl)propanoate (3.10 kg, 5.14 mol) in 1.3 M HCl in acetonitrile prepared from hydrogen chloride (1.31 kg 35.9 mol) and acetonitrile (21.7 kg) was stirred for 12-24 hours at 29-33° C. A conversion of ($^2H_5$) ethyl (25)-2-[(25)-3-{4-[bis(2-chloroethyl)amino]phenyl}-2-{[(tert-butoxy)carbonyl]-amino}propanamido]-3-(4-fluorophenyl)propanoate into ($^2H_5$)ethyl (25)-2-[(25)-2-amino-3-{4-[bis(2-chloroethyl)amino]phenyl}propanamido]-3-(4-fluorophenyl)propanoate hydrochloride of minimum 99.0% (HPLC) was obtained (HPLC conditions were as follows: sample solvent DMSO acetonitrile, 1:9 (v/v), Waters, Atlantic $T_3$ (3μ, 4.6×150 mm) column, 10-90-10% B gradient over 23 min, flow of 1 mL/min, mobile phase A: 500 μL phosphoric acid 85% in 1.0 L MQ-water, mobile phase B: 500 phosphoric acid 85% in 1.0 acetonitrile, with UV detection at 262 nm.).

The reaction mixture was subjected to polish filtration and diluted with acetonitrile (68.9 kg). Distillation at reduced pressure was then performed using a jacket temperature of 45° C. When the volume of the reaction mixture was 86 L, acetonitrile (22.7 kg) was added and the distillation continued. When 86 L of reaction mixture was left, acetonitrile (22.7 kg) was added and the distillation continued. When the volume in the reactor was 86 L, acetonitrile (22.7 kg) was added and distillation continued until a volume of 86 L in the reactor was reached.

tert-Butyl methyl ether (68.4 kg) was added over a period of 25-45 min at 35-45° C. followed by cooling to 22-28° C. After stirring at this temperature for 60-120 min, crude ($^2H_5$)ethyl (2S)-2-[(2S)-2-amino-3-{4-[bis(2-chloroethyl)amino]phenyl}propanamido]-3-(4-fluorophenyl)propanoate hydrochloride was filtered off and washed with tert-butyl methyl ether (12.5 kg). The crude material was dried in vacuum in the reactor using a jacket temperature set point of 30° C.

Acetonitrile (84.0 kg) was added and the resulting suspension is stirred for 30-90 min at 48-54° C. followed by cooling to 40-45° C. tert-Butyl methyl ether (74.6 kg) was added over a period of 40-70 min at 38-45° C. followed by cooling to 22-28° C. After stirring at this temperature for 60-120 min, crude ($^2H_5$)ethyl (2S)-2-[(2S)-2-amino-3-{4-[bis(2-chloroethyl)amino]phenyl}propanamido]-3-(4-fluorophenyl)propanoate hydrochloride was filtered off and washed with tert-butyl methyl ether (14.0 kg). Drying in vacuum at 30-35° C. provided ($^2H_5$)ethyl (2S)-2-[(2S)-2-amino-3-{4-[bis(2-chloroethyl)amino]phenyl}propanamido]-3-(4-fluorophenyl)propanoate hydrochloride (OPD5 in its HCl salt form) (2.5 kg, 90%) as a white to off-white solid. HPLC: retention time 9.0 min.

The invention claimed is:

1. A liquid pharmaceutical formulation comprising the following components:
- i) melflufen, or a salt thereof; and
- ii) propylene glycol;

in which the melflufen, or a salt thereof, is at a concentration of about 10 mg/mL to about 50 mg/mL, and in which the formulation is substantially free from organic solvents that are not propylene glycol or polyethylene glycol (PEG), and wherein the formulation is substantially free from alkaline earth metal salts.

2. The pharmaceutical formulation of claim 1, wherein the melflufen, or salt thereof, is at a concentration of about 15 mg/mL to about 25 mg/mL.

3. The pharmaceutical formulation of claim 1, consisting essentially of melflufen, or a salt thereof, propylene glycol, and one or more additional therapeutic agent(s) selected from the group consisting of prednisone, prednisolone, dexamethasone, thalidomide, lenalidomide, pomalidomide, bortezomib, carfilzomib, ixazomib, panobinostat, melphalan, cyclophosphamide, bendamustine, doxorubicin, daratumumab, and elotuzumab.

4. The pharmaceutical formulation of claim 1, further comprising one or more physiologically acceptable solution(s) selected from the group consisting of a glucose solution, a saline solution, and a mixture of a glucose solution and a saline solution.

5. The pharmaceutical formulation of claim 1, further comprising one or more additional therapeutic agent(s) selected from the group consisting of bortezomib, carfilzomib, ixazomib, thalidomide, lenalidomide, pomalidomide, melphalan, cyclophosphamide, and bendamustine.

6. The pharmaceutical formulation of claim 1, wherein the melflufen is in the form of its hydrochloride, ethanesulfonate, maleate or p-toluenesulfonate salt.

7. The pharmaceutical formulation of claim 1, wherein the melflufen is deuterated melflufen.

8. The pharmaceutical formulation of claim 1, wherein the melflufen is OPD-5:

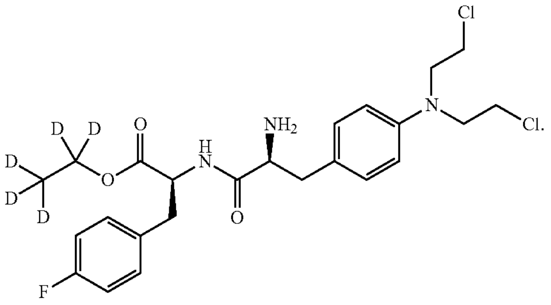 [SMILES: [2H]C([2H])([2H])C([2H])([2H])OC(=O)[C@H](Cc1ccc(F)cc1)NC(=O)[C@@H](N)Cc1ccc(N(CCCl)CCCl)cc1]

9. The pharmaceutical formulation of claim 1, which comprises less than about 1% w/v of an organic solvent other than propylene glycol or PEG and less than about 1% w/v of alkaline earth metal salt(s).

10. The pharmaceutical formulation of claim 1, which comprises less than about 0.5% w/v of an organic solvent other than propylene glycol or PEG and less than about 0.5% w/v of alkaline earth metal salt(s).

11. The pharmaceutical formulation of claim 1, which comprises less than about 0.1% w/v of an organic solvent other than propylene glycol or PEG and less than about 0.1% w/v of alkaline earth metal salt(s).

12. A method for the treatment of a cancer selected from the group consisting of multiple myeloma, breast cancer, lung cancer, ovarian cancer, leukemias and lymphomas, comprising administering an effective amount of the pharmaceutical formulation of claim 1 to a subject in need thereof.

13. The method of claim 12, wherein the pharmaceutical formulation is directly administered to the subject in need thereof.

14. The method of claim 12, wherein the subject is further treated with a conventional chemotherapy agent selected from the group consisting of melphalan, cyclophosphamide, bendamustine, and doxorubicin.

15. A method for the treatment of amyloidosis, comprising administering an effective amount of the pharmaceutical formulation of claim 1 to a subject in need thereof.

16. A method for preparing the pharmaceutical formulation of claim 1 comprising dissolving melflufen, or a salt thereof, in propylene glycol.

17. A method for storing melflufen, or a salt thereof, comprising the steps of preparing a pharmaceutical formulation according to claim 1, and storing the pharmaceutical formulation at a temperature of about −90 to 25° C.

18. A kit for preparing the pharmaceutical formulation of claim 1, comprising melflufen, or a salt thereof; and propylene glycol separate from the melflufen or salt thereof.

* * * * *